US012708698B2

(12) United States Patent
Germaini et al.

(10) Patent No.: US 12,708,698 B2
(45) Date of Patent: Aug. 18, 2026

(54) FORMULATION COMPRISING A PHOSPHOCALCIC CEMENT AND A PHYSICAL AND/OR COVALENT HYDROGEL OF POLYSACCHARIDES, PRINTABLE AND HAVING DUCTILE MECHANICAL PROPERTIES FOR BONE REGENERATION/BONE REPAIR

(71) Applicants: INSERM (Institut National de la Santé et de la Recherche Médicale), Paris (FR); Nantes Université, Nantes (FR); CHU Nantes, Nantes (FR)

(72) Inventors: Marie-Michèle Germaini, Nantes (FR); Pierre Weiss, Nantes (FR); Pierre Corre, Montbert (FR); Hélène Gautier, Les Sorinieres (FR)

(73) Assignees: INSTITUT NATIONAL DE LA SANTE ET DE LA RECHERCHE MEDICALE (INSERM), Paris (FR); Nantes Université, Nantes (FR); CHU Nantes, Nantes (FR)

( * ) Notice: Subject to any disclaimer, the term of this patent is extended or adjusted under 35 U.S.C. 154(b) by 657 days.

(21) Appl. No.: 17/996,399

(22) PCT Filed: Apr. 16, 2021

(86) PCT No.: PCT/EP2021/059945

§ 371 (c)(1),
(2) Date: Oct. 17, 2022

(87) PCT Pub. No.: WO2021/209616

PCT Pub. Date: Oct. 21, 2021

(65) Prior Publication Data

US 2023/0201422 A1 Jun. 29, 2023

(30) Foreign Application Priority Data

Apr. 17, 2020 (EP) .................................... 20315185

(51) Int. Cl.

| | |
|---|---|
| *A61L 27/38* | (2006.01) |
| *A61L 27/20* | (2006.01) |
| *A61L 27/46* | (2006.01) |
| *A61L 27/52* | (2006.01) |
| *A61L 27/54* | (2006.01) |

(52) U.S. Cl.
CPC ........... *A61L 27/3847* (2013.01); *A61L 27/20* (2013.01); *A61L 27/46* (2013.01); *A61L 27/52* (2013.01); *A61L 27/54* (2013.01)

(58) Field of Classification Search
None
See application file for complete search history.

(56) References Cited

U.S. PATENT DOCUMENTS

| | | | | |
|---|---|---|---|---|
| 2018/0222655 | A1 * | 8/2018 | Grabowski | B65D 5/5021 |
| 2021/0260249 | A1 * | 8/2021 | Alimperti | A61L 27/446 |

FOREIGN PATENT DOCUMENTS

| | | | | |
|---|---|---|---|---|
| CN | 109381749 A | * | 2/2019 | B33Y 70/00 |
| WO | 2011/089267 A1 | | 7/2011 | |
| WO | 2013/171736 A1 | | 11/2013 | |

OTHER PUBLICATIONS

Machine translation for CN 109 381 749 A, Feb. 26, 2019 (Year: 2019).*
D'Este et al.; "Hydrogels in calcium phosphate moldable and injectable bone substitutes: Sticky excipients or advanced 3-D carriers?"; Acta Biomaterialia, vol. 9, No. 3, Mar. 1, 2013, pp. 5421-5430.
Zhai et al.; "The application of hyaluronic acid in bone regeneration"; International Journal of Biological Macromolecules, vol. 151, Nov. 18, 2019, pp. 1224-1239.
Leng et al.; "Material-based therapy for bone nonunion"; Materials & Design, vol. 183, Aug. 29, 2019.
Begam et al.; "Strategies for delivering bone morphogenetic protein for bone healing"; Materials Science and Engineering C, vol. 70, Sep. 30, 2016, pp. 856-869.

* cited by examiner

*Primary Examiner* — Carlos A Azpuru
*Assistant Examiner* — Casey S Hagopian
(74) *Attorney, Agent, or Firm* — WCF IP

(57) ABSTRACT

The present invention relates to the use of a formulation comprising a phosphocalcic cement and a physical and/or covalent hydrogel of polysaccharides for 3D printing, more particularly for bone regeneration and/or bone repair. The present invention also relates to a kit for 3D printing of bone implants comprising a phosphocalcic cement and a physical and/or covalent hydrogel of polysaccharides as well as to a method to prepare a formulation for 3D printing comprising a step of mixing a phosphocalcic cement and a physical and/or covalent liquid hydrogel precursor of polysaccharides.

20 Claims, 20 Drawing Sheets

Figure 10:
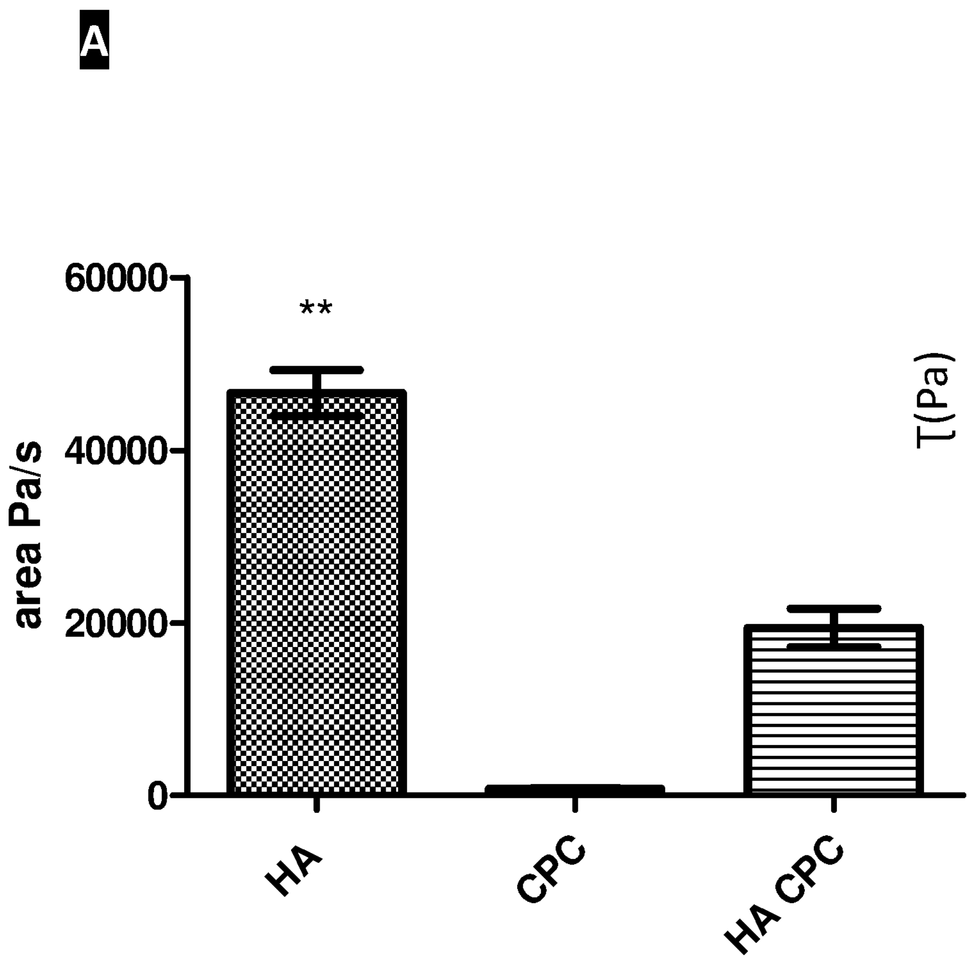

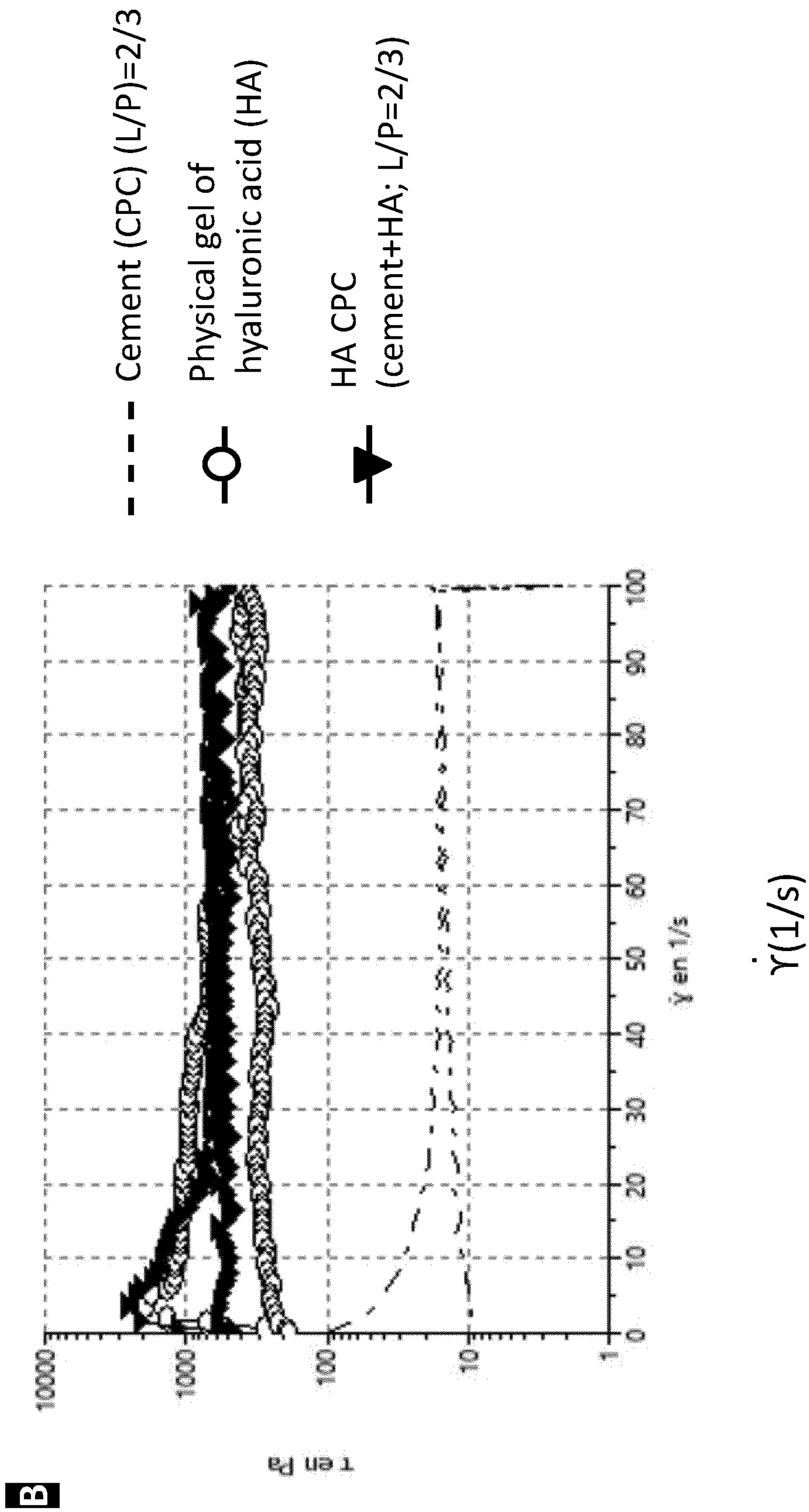
FIG.10 End

Figure 11:
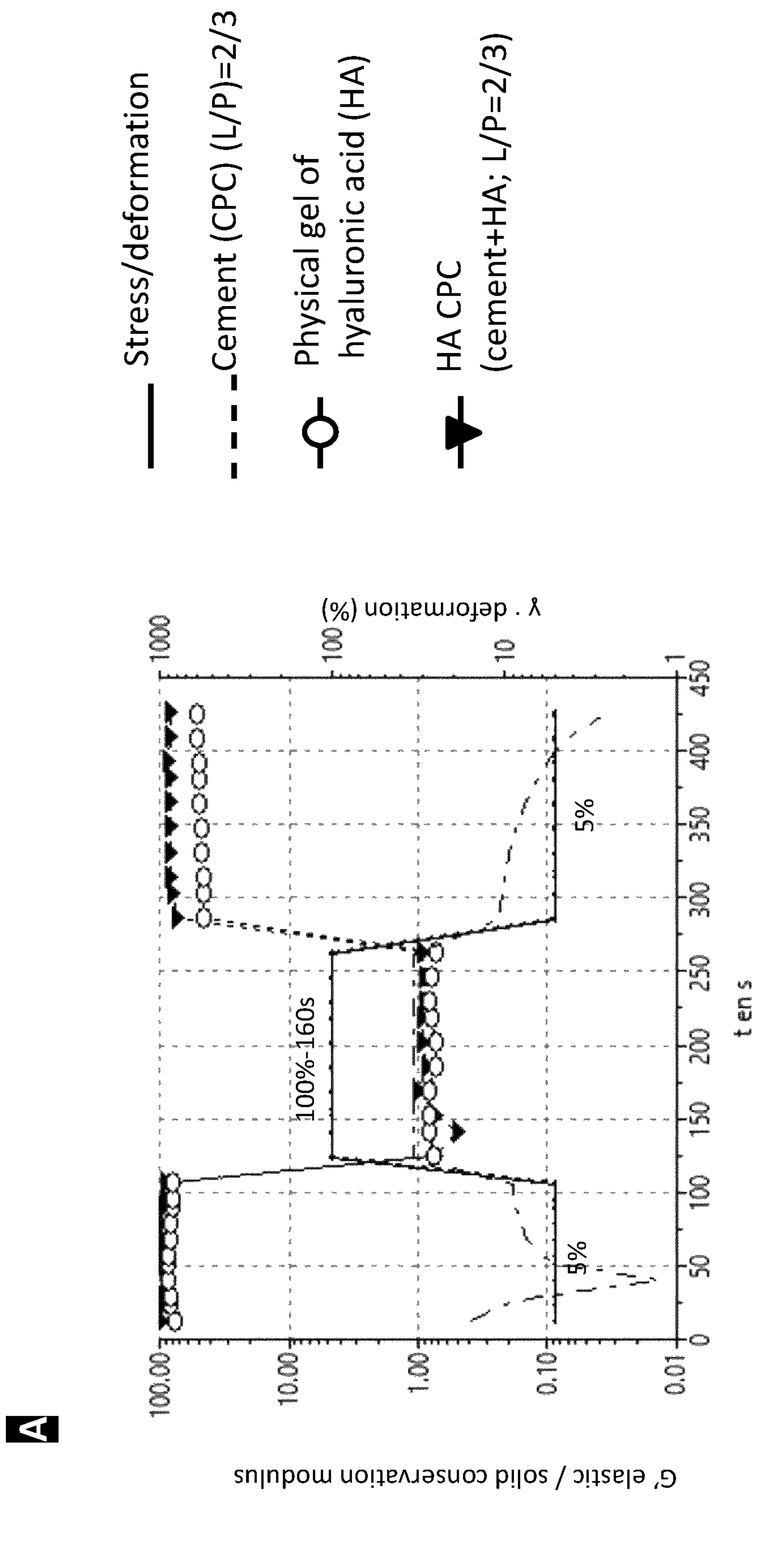

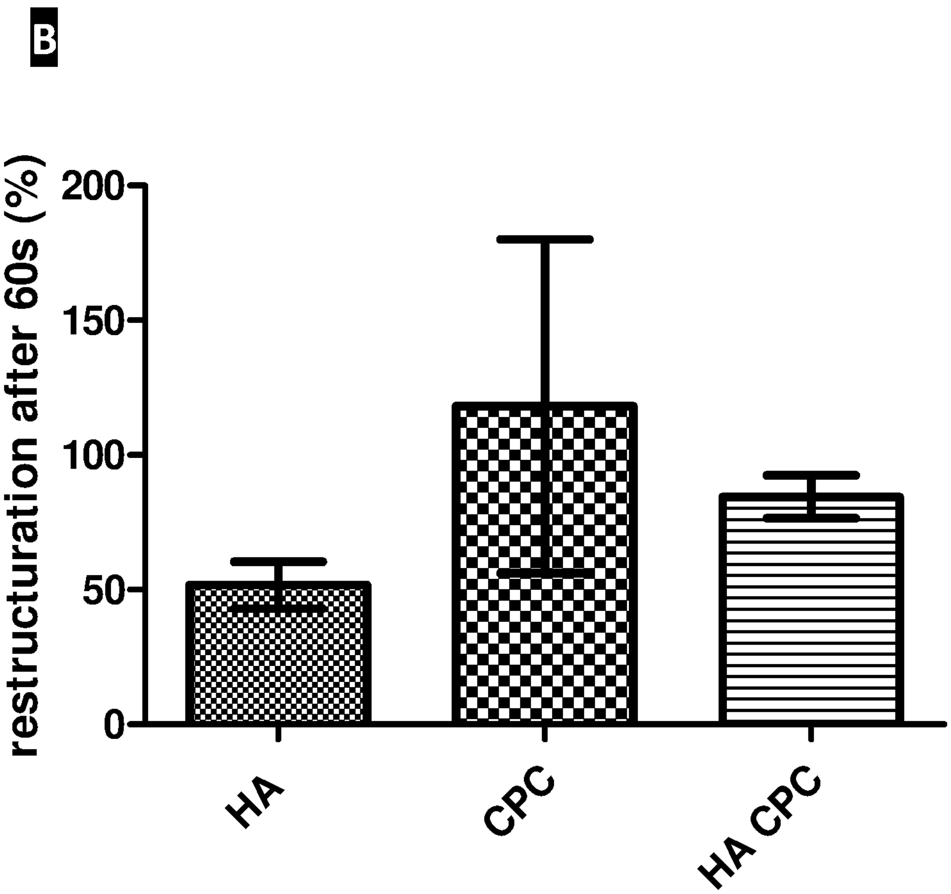
FIG.11 end

Figure 12:
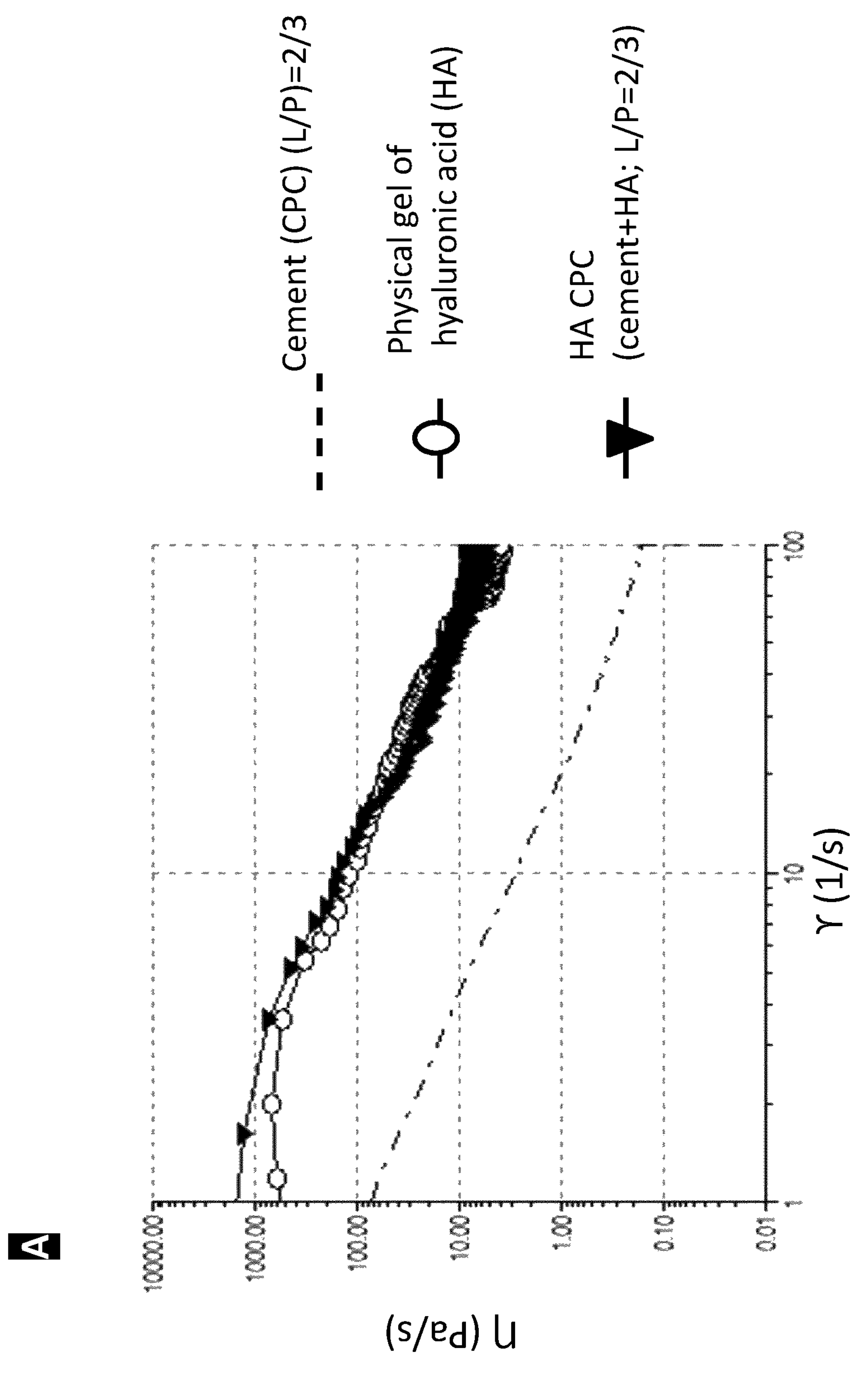
Figure 12:
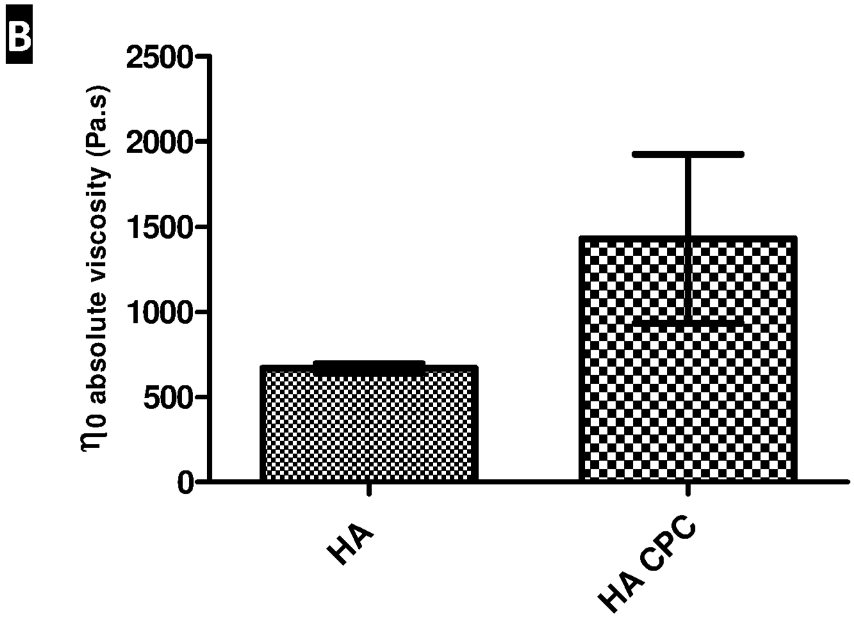
Figure 12:
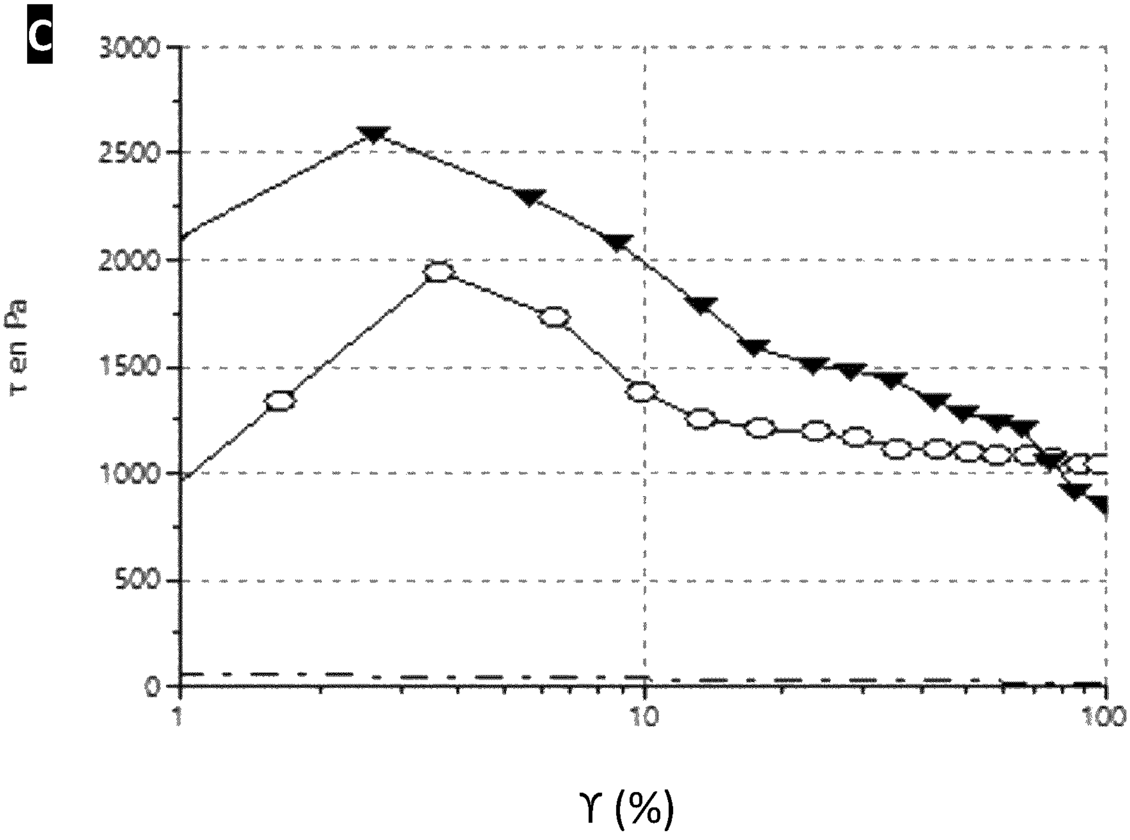

D
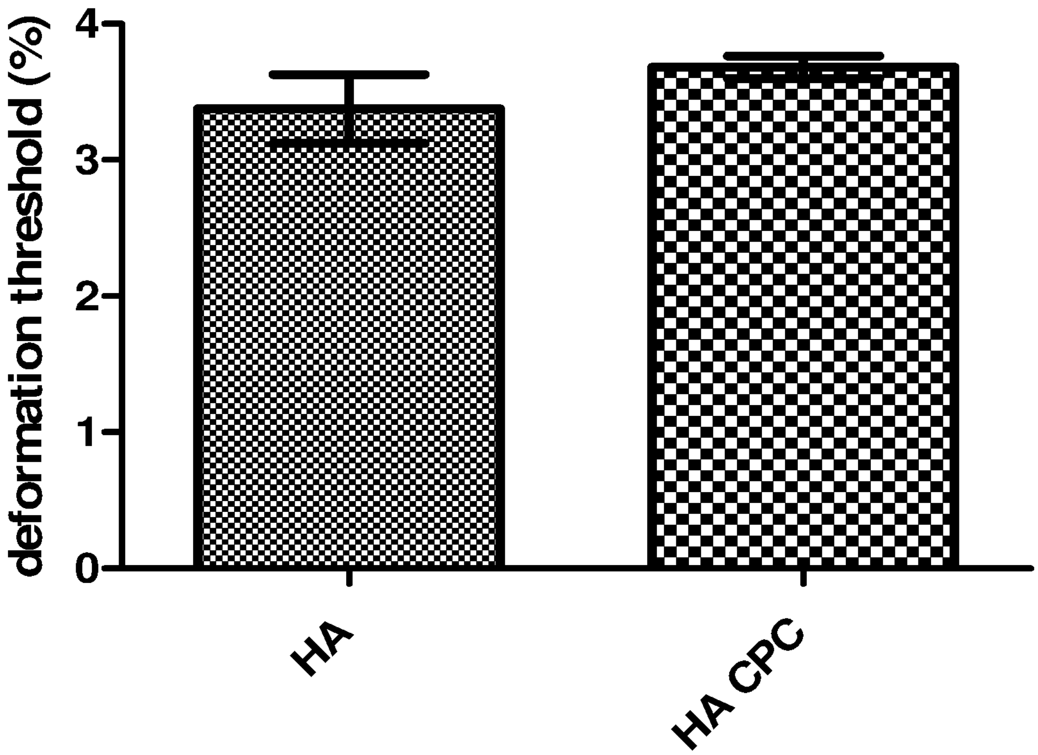
FIG.12 end

FORMULATION COMPRISING A PHOSPHOCALCIC CEMENT AND A PHYSICAL AND/OR COVALENT HYDROGEL OF POLYSACCHARIDES, PRINTABLE AND HAVING DUCTILE MECHANICAL PROPERTIES FOR BONE REGENERATION/BONE REPAIR

The present invention relates to the use of a formulation comprising a phosphocalcic cement and a physical and/or covalent hydrogel of polysaccharides for 3D printing, more particularly for bone regeneration and/or bone repair. The present invention also relates to a kit for 3D printing of bone implants comprising a phosphocalcic cement and a physical and/or covalent hydrogel of polysaccharides as well as to a method to prepare a formulation for 3D printing comprising a step of mixing a phosphocalcic cement and a physical and/or covalent liquid hydrogel precursor of polysaccharides.

A clinical issue is today the repair of bone, without recourse to autologous bone grafting.

Several clinical problems and limits are encountered in the current management of bone defects, and there is thus a need for biomaterials having properties that should mimic the mechanical characteristics of bone.

In 3D printing, there is a huge impact of rheological and mechanical properties of the composition used for printing, notably for the preparation of bone implants which should be able to perfectly fill the complex shape of the bone defect.

The goal of the invention was thus to create a 3D printable formulation for use for bone repair, especially adapted to the complex shape of the bone defect, allowing vascular colonization, bone repair and resorption of the material.

Several characteristics are necessary for bone regeneration: biocompatibility, resorbability, osteoconductivity, osteoinduction and osteointegration, and control of inflammatory properties.

At the same time, rheological properties should allow the three-dimensional impression of implants for bone regeneration.

The formulation has to be sterializable without drastic alteration of its chemical composition, and most importantly the formulation has to be not-brittle with ductile properties (making it more friendly handling by the user, especially in the first step of the preparation of the printing and designing of the implant).

It should keep adapted resistance to fracture in compression and bending after sterilization and can be used to produce architectures with macro-porosities adapted to cells and bone ingrowth and nano porosity adapted to integrate growth factors.

The requirements for developing 3D printed formulation with full bone biomimetic properties is thus a real challenge.

The inventors of the present invention have been able to develop an innovative and easy to prepare formulation that meets all the mechanical, biological and regulatory requirements for bone repair (injectable, printable, cohesive, ductile, biocompatible, biodegradable and sterilizable).

The invention thus relates to the use of a formulation comprising a phosphocalcic cement and a physical and/or covalent hydrogel of polysaccharides for 3D printing.

In particular, said formulation is used for 3D printing of bone implants.

Said formulation should allow to limit the morbidity of the operative process, personalized medicine, and the design of a controlled internal architecture in order to promote bone regrowth, control biodegradation, cell infiltration and vascularization to the center of the implant.

The invention also relates to a kit for 3D printing of bone implants comprising:

(i) a phosphocalcic cement; and (ii) a physical and/or covalent hydrogel of polysaccharides.

It further relates to a method to prepare a formulation for 3D printing comprising a step of mixing a phosphocalcic cement and a physical and/or covalent liquid precursor hydrogel of polysaccharides.

Phosphocalcic cement (CPC) are well known in the art. According to the invention, a "calcium phosphate cement" or "phosphocalcic cement" (or CPC) is a cement wherein the pulverulent solid phase (or powder component) is made of a calcium phosphate compound or a mixture of calcium and/or phosphate compounds. Varying compositions of CPC are commercially available. In the context of the present invention, the term "phosphocalcic" or "calcium phosphate" refers to minerals containing calcium ions ($Ca^{2+}$) together with orthophosphate ($PO_4^{3-}$), metaphosphate or pyrophosphate ($P_2O_7^{4-}$) and occasionally other ions such as hydroxide ions or protons.

In particular, the phosphocalcic cement according to the invention is a tricalcium phosphate cement. More particularly, said tricalcium phosphate cement has alpha tricalcium phosphate as a precursor.

Tricalcium phosphate (TCP) has the formula $Ca_3(PO_4)_2$ and is also known as calcium orthophosphate, tertiary calcium phosphate, tribasic calcium phosphate or bone ash. α-TCP has the formula $\alpha\text{-}Ca_3(PO_4)_2$.

In one embodiment, the cement used in the formulation according to the invention is in powder form, more particularly in the form of grains of size less than 40 μm, and even more particularly less than 20 μm.

These sizes are an average size.

In the context of the present invention, the term "average size" (or "average grain size" or "mean particle size") denotes the mean equivalent diameter of said particles measured by LASER diffraction analysis.

The cement used in the formulation according to the invention can be prepared by a chemical reaction between two phases, a solid and a liquid which, when mixed, form a paste which progressively sets and hardens into a solid mass; this is similar to the cements used in civil engineering. The solid phase comprises one or several calcium phosphate (CaP) compounds. Water or a calcium- or phosphate-containing solution is used as liquid which may contain chitosan, alginate or citric acid to allow the dissolution of the initial CaP compounds until the over-saturation of the solution, thus inducing the reprecipitation of crystals. The hardening of the cement takes place through the entanglement of needle-like or plate-like crystals. Currently, there are only two possible final products for the CPC reaction: brushite (Dicalcium Phosphate Dihydrate: DCPD) or apatite such as hydroxyapatite or calcium-deficient hydroxyapatite (CDHA) closer to the chemical composition of natural bone]. There are two major routes for synthesizing α-TCP:

(1) thermal transformation of a single precursor with a molar ratio Ca/P≈1.5 (either CDHA; amorphous calcium phosphate, ACP; or β-TCP);

(2) solid-state reaction of a mixture of solid precursors at high temperatures.

For example, α-TCP powder can be synthesize by a high-temperature solid-state reaction between DCPA and calcium carbonate, as follows:

$$2\ CaHPO_4+CaCO_3\rightarrow\alpha\text{-}Ca_3(PO_4)_2+CO_2+H_2O.$$

For example, a tricalcium phosphate cement can be prepared by mixing 2 $CaHPO_4$ and $CaCO_3$ with a three-dimensional mixer, submitting the obtained product to isostatic compression (for example at 120 MPa), further to a calcination step (for example at 1360° C. during 15 hours), a compressed air quenching, grinding stages (for example submitting the mixture to a centrifugal crusher followed by a mortar crusher) and a final sieving step.

Size sieves can be for example of 40 and/or 20 μm.

As mentioned above, the hydrogel according to the invention is a physical and/or covalent hydrogel of polysaccharides.

The term "hydrogel" means a network of polymer chains that are water-insoluble, in which water is the dispersion medium.

A "physical" hydrogel is a hydrogel that can undergo a reversible transition from liquid (solution) to a gel in response to a change in environmental conditions such as temperature, ionic concentration, pH, or other conditions such as mixing of two components. The network is formed through molecular entanglements and/or secondary forces including hydrogen bonding, hydrophobic forces and electrostatic interactions.

A "covalent" hydrogel use covalent bonding that introduces mechanical integrity and degradation resistance compared to other weak material. Chemical crosslinking relies on the formation of covalent bonds between reacting groups grafted to the polymer backbone that will crosslink under specific conditions. Generally, carboxyl, hydroxyl and amine are the most targeted groups. Organo-mineral moieties like silanols can also be used.

As used herein, the term "polysaccharide" means a polymer made up of many monosaccharides joined together by glycosidic bonds. Natural and synthetic polysaccharides are included. Examples of polysaccharide are cellulose and derives thereof, for instance hydroxypropylmethylcellulose (HPMC), hydroxyethylcellulose (HEC), and carboxymethylcellulose (CMC), pectin, chitosan and hyaluronic acid.

The hydrogel may contain either only one kind of polysaccharide or polysaccharides of different nature, preferably two different polysaccharides.

In particular, polysaccharides of the hydrogel according to the invention are hyaluronic acid and/or chitosan.

Hyaluronic acid is a well-known component. It is the primary component of the extracellular matrix of human connective tissues. Hyaluronic acid is a high molecular weight linear polysaccharide of alternating D-glucuronic acid and N-acetyl-D-glucosamine that constitutes the backbone of the ECM. It can be degraded by hyaluronidases, either added exogenously or produced by cells. Depending of the molecular weight, hyaluronic acid can be anti inflammatory.

Chitosan is also a well known component. It is a linear polysaccharide composed of randomly distributed β-(1→4)-linked D-glucosamine (deacetylated unit) and N-acetyl-D-glucosamine (acetylated unit). It is made by treating the chitin shells of shrimp and other crustaceans with an alkaline substance, like sodium hydroxide.

In particular, the polysaccharide used in the context of the present invention is hyaluronic acid and/or chitosan, more particularly hyaluronic acid.

In one embodiment, the hydrogel is a physical hydrogel.

In one example, the hydrogel is a physical hydrogel comprising 2 to 4% w/v of hyaluronic acid and/or chitosan.

In particular, the hydrogel is a physical hydrogel comprising hyaluronic acid.

Still particularly, the physical hydrogel comprises hyaluronic acid with a molecular weight of comprised between 420 kDa and 2.88 MDA.

A dalton (Da) is a mass unit defined as being equal to one-twelfth of the mass of a carbon 12 atom, a mass which will subsequently be estimated from a mixture of several isotopes (mainly carbon 12 and carbon 13, respectively having 6 and 7 neutrons in addition to the 6 protons like any carbon atom). One dalton is, with quite good accuracy, the mass of a hydrogen atom, the exact value being 1.00794 amu (atomic mass unit). The kilodalton (kDa) is equal to 1,000 Da. The megadalton (MDa) is equal to 1,000 kDa.

Within the scope of the present invention, the masses mentioned in Da or kDa are determined by any method usually used by one skilled in the art (size exclusion chromatography for example).

In another embodiment, the hydrogel is a covalent hydrogel, in particular a covalent hydrogel comprising silylated polysaccharides, for example silylated hyaluronic acid and/or silylated chitosan. More particularly, said covalent hydrogel comprises from 2 to 4 w/v of silated hyaluronic acid and/or silated chitosan.

As used herein, the term "silylated polysaccharide" means any organic or synthetic polysaccharide onto which are grafted an organo-mineral silyl function, preferably an alkoxysylane. Silylation allows the formation of covalent bonds between the polysaccharides constituting the hydrogel as a function of pH. The silylated biomolecules are thus able to form a pH-dependent self-reticulating hydrogel.

A physical hydrogel as used in the formulation according to the invention can be prepared by dissolving the lyophilized polysaccharide, for example hyaluronic acid, in a aqueous solution, for example of pH ranging 7-8 or by dissolving the powder of polysaccharide, for example chitosan, in an aqueous acidic solution, for example of pH ranging 1-3.

A covalent hydrogel as used in the formulation according to the invention can be prepared by for example according to the method described in WO2011089267.

For example, in the case of a covalent hydrogel comprising silylated hyaluronic acid, amidation between the carboxylic acid of hyaluronic acid and the primary amine of aminopropyltriethoxysilane (APTES) can be conducted. To facilitate this reaction, an activating agent, such as 4-(4,6-Dimethoxy-1,3,5-triazin-2-yl)-4-methylmorpholinium chloride (DMTMM), can be used.

The ratio hydrogel/cement in the formulation used in the context of the invention can vary.

In one embodiment, the ratio hydrogel/cement of the formulation is of 2:3 w/w.

As already mentioned, the formulation used for 3D printing is sterilizable without alteration of its chemical composition, not brittle, and has ductile properties.

The invention also relates to a method to prepare such formulation.

It thus relates to a formulation for 3D printing comprising a step of mixing a phosphocalcic cement and a physical and/or covalent liquid precursor hydrogel of polysaccharides.

The definitions of "formulation", "phosphocalcic cement" and "physical and/or covalent hydrogel of polysaccharides" previously mentioned apply for the method according to the invention.

By "precursor hydrogel" is meant the viscous solution of macromolecules before crosslinking and becoming a gel (insoluble solid)

The formulation according to the invention can be obtained by mixing the cement and the hydrogel previously described.

In particular, said method comprises the step of mixing the phosphocalcic cement, for example α-TCP particles, and a physical and/or covalent liquid hydrogel precursor of polysaccharides, said liquid hydrogel precursor comprising in particular hyaluronic acid and/or chitosan.

In one embodiment, grains of the powder have a size less than 40 μm, in particular less than 20 μm.

The mixture can be prepared by any method known by the man skilled in the art such as handling blending of the powder with the hydrogel.

In one embodiment, the method to prepare a formulation for 3D printing according to the invention comprises a step of adding active molecules and/or cells within the formulation.

In another embodiment, the method according to the invention also comprises a sterilization step, wherein in particular the cement and the hydrogel of the formulation can be sterilized by different means and separately.

In one embodiment, the formulation is prepared in a sterile room or a PSM.

The invention also relates to a method for 3D printing, in particular for 3D printing of bone implants comprising:

- (i) preparing a formulation comprising a phosphocalcic cement, for example α-TCP powder, and a physical and/or covalent hydrogel of polysaccharides, said hydrogel comprising in particular hyaluronic acid and/or chitosan as described herein;
- (ii) 3D printing of said formulation; and optionally
- (iii) inserting the implant obtained further to step (ii) in a bone cavity.

The formulation described herein is used for 3D printing.

The 3D printed formulation can be used for bone repair, augmentation, reconstruction, regeneration, and treatment of bone disease.

More particularly, the formulation according to the invention is used for bone regeneration and/or bone repair, even more particularly, in the context of vertical bone augmentation, complex geometries, large critical size bone defects, following congenital diseases or to fill bone defects following tumor resections.

The formulation according to the invention may be used in many applications, especially surgical applications.

The present invention also relates to an implant comprising a formulation as defined in the context of the invention. In particular, said formulation is 3D printed.

In particular, said implant is a bone implant.

This implant may be used to repair, restore, or augment bone, and/or to fill the bone cavity.

In one embodiment, the implant further comprises active molecules and/or cells.

For example, such active molecules are chosen from BMP2 or VEGF, in particular from growth factors.

This implant can release these active molecules in a controlled manner.

The invention also relates to a method for bone repair and/or bone regeneration comprising:

- (i) preparing a formulation comprising a phosphocalcic cement, for example α-TCP powder, and a physical and/or covalent hydrogel of polysaccharides, said hydrogel comprising in particular hyaluronic acid and/or chitosan;
- (ii) 3D printing of said formulation; and optionally
- (iii) inserting the implant obtained further to step (ii) in a bone cavity, in particular a complex bone cavity, more particularly a complex bone cavity with slight undercuts.

In one embodiment, the cement and the hydrogel are sterilized in a sterile environment.

Still particularly, the cement and the hydrogel of the formulation can be sterilized by different means and separately.

For example, the formulation is prepared in a sterile room or a PSM.

In another embodiment, the implant is sterilized before insertion in a way compatible with the maintain of its mechanical and biological properties.

Said step can be performed for example by a short cycle of steam sterilization, more particularly bowie dick can be used (for example at 134° C. during 3.5 min). This is the current cycle used for medical device.

In one embodiment, after sterilization of the implant, the method also comprises a step of adding active molecules and/or cells within the implant.

3D printing is generally associated with a host of related technologies used to fabricate physical objects from computer generated, e.g. computer-aided design (CAD), data sources "3D printer" is defined as "a machine used for "3D printing" and "3D printing" is defined as "the fabrication of objects through the deposition of a material using a print head, nozzle, or another printer technology."

"Printing" is defined as depositing of a material, here the formulation according to the invention, using a print head, nozzle, or another printer technology.

In this disclosure "3D or three dimensional printed formulation or implant" means a formulation or implant obtained by 3D printing.

In general, all 3D printing processes have a common starting point, which is a computer generated data source or program which may describe an object. The computer generated data source or program can be based on an actual or virtual object. For example, an actual object can be scanned using a 3D scanner and scan data can be used to make the computer generated data source or program. Alternatively, the computer generated data source or program may be designed using a computer-aided design software.

The computer generated data source or program is typically converted into a standard tessellation language (STL) file format; however other file formats can also or additionally be used. The file is generally read into 3D printing software, which takes the file and optionally user input to separate it into hundreds, thousands, or even millions of "slices." The 3D printing software typically outputs machine instructions, which may be in the form of G-code, which is read by the 3D printer to build each slice. The machine instructions are transferred to the 3D printer, which then builds the object, layer by layer, based on this slice information in the form of machine instructions. Thicknesses of these slices may vary.

In particular, the 3D printer is an extrusion 3D printer.

An extrusion 3D printer is a 3D printer where the material is extruded through a nozzle, syringe or orifice during the manufacturing process. Material extrusion generally works by extruding material through a nozzle, syringe or orifice to print one cross-section of an object, which may be repeated for each subsequent layer. The extruded material bonds to the layer below it during cure of the material.

In one embodiment, the invention also relates to a method for preparing a 3D printed implant, wherein the formulation according to the invention is 3D printed with an extrusion 3D printer.

The formulation is extruded through a nozzle. The nozzle may be heated to aid in dispensing the addition formulation.

The formulation to be dispensed through the nozzle may be supplied from a cartridge-like system. The cartridge may include a nozzle or nozzles with an associated fluid reservoir or fluids reservoirs. It is also possible to use a coaxial two cartridges system with a static mixer and only one nozzle. Pressure will be adapted to the fluid to be dispensed, the associated nozzle average diameter and the printing speed.

The extrusion printing technic according to the invention is advantageous as it avoids the addition of chemical reagents which may be cytotoxic.

The printing with a formulation according to the invention is easy and does not require a debinding step nor sintering.

The invention also relates to a kit for 3D printing of bone implants comprising:

(i) a phosphocalcic cement; and (ii) a physical and/or covalent hydrogel of polysaccharides.

The definitions of "phosphocalcic cement", "physical and/or covalent hydrogel of polysaccharides", "3D printings" and "bone implants" previously mentioned apply for the kit according to the invention.

In one embodiment, the hydrogel of the kit is a physical hydrogel comprising 4% w/v of hyaluronic acid and/or chitosan.

In another embodiment, the hydrogel of the kit is a covalent hydrogel comprising 2 to 4% w/v of silated hyaluronic acid and/or silated chitosan.

All the embodiments mentioned in the context of the present invention can be combined.

The invention will be further illustrated by the following figures and examples.

FIGURES

Figure 1:
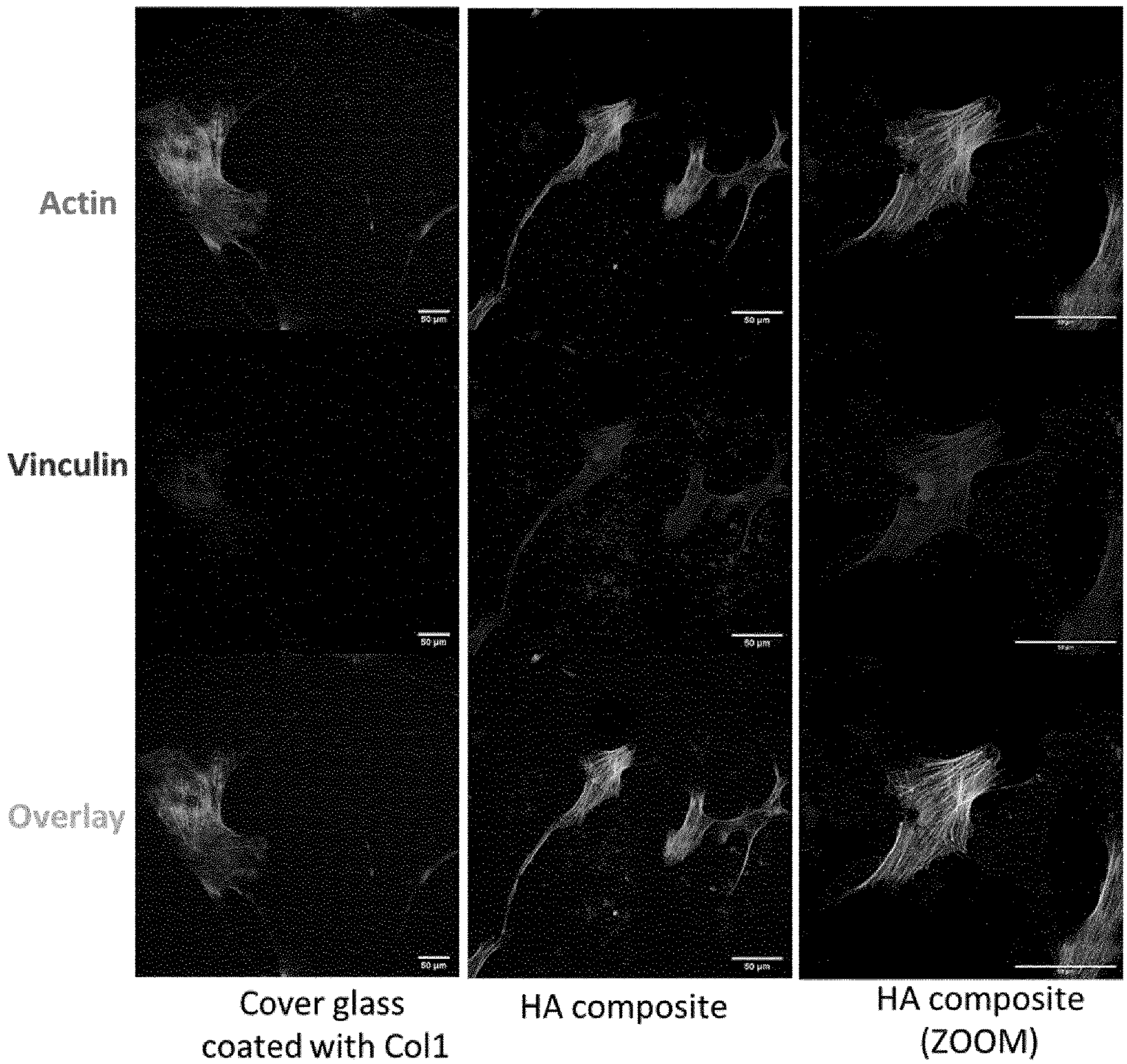

FIG. 1: confocal microscopy image of MSC seeded during 16 days on cover glass coated with collA1 or on HA composite cement and labelled with actin and vinculin.

Figure 2:
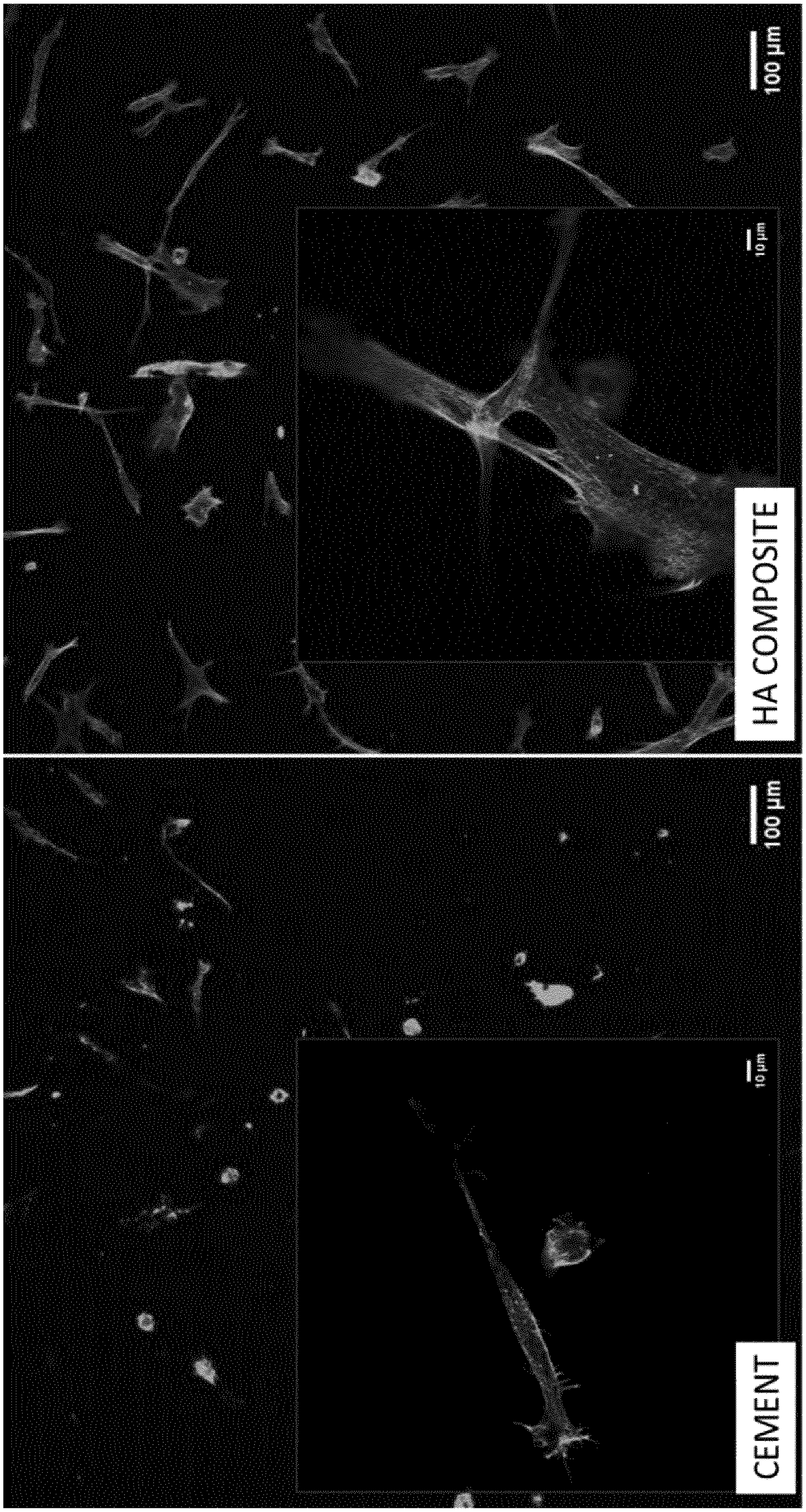

FIG. 2: confocal microscopy image of MSC seeded on cement or on HA composite cement during 4 days and labelled with phalloidin.

Figure 3:
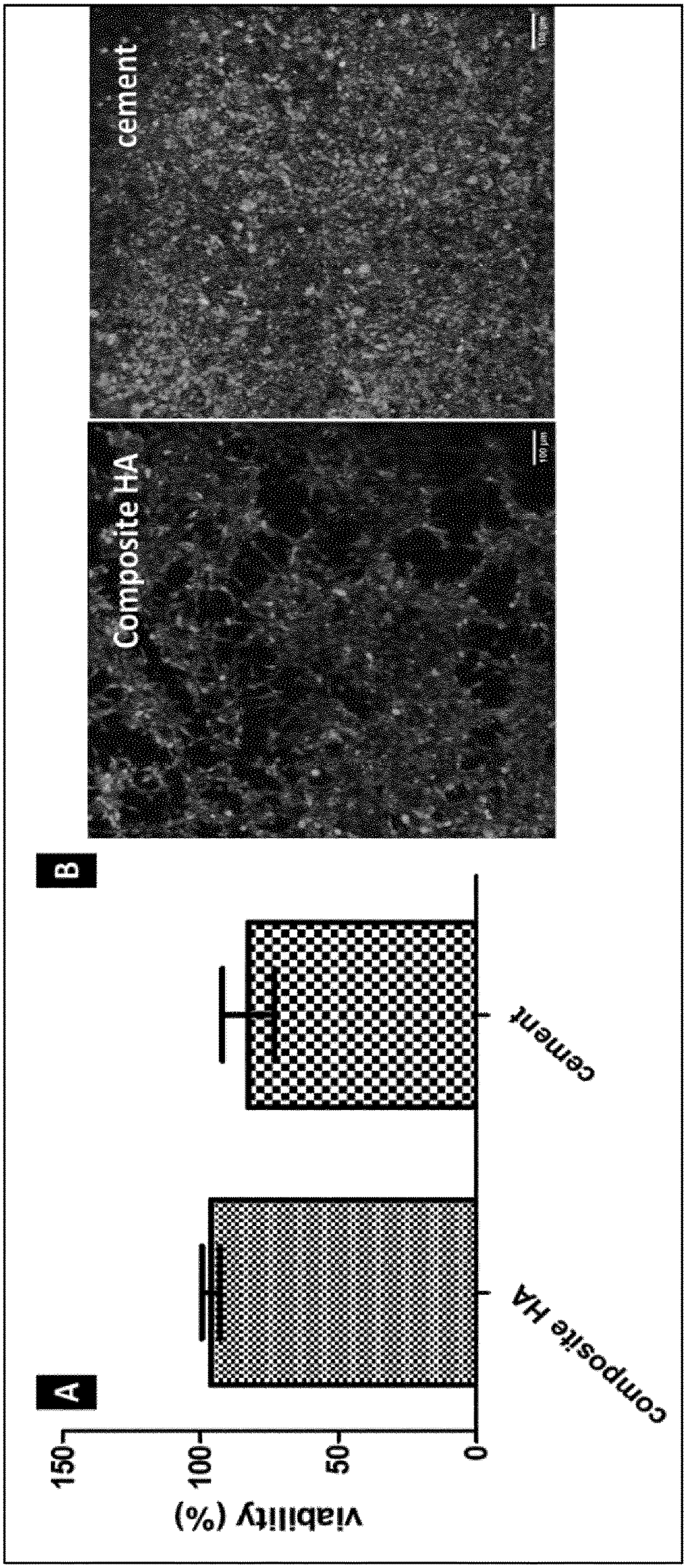

FIG. 3: rate of viability of Fibroblast cell line L929 after 4 days of culture on composite HA cement or on cement.

Figure 4:
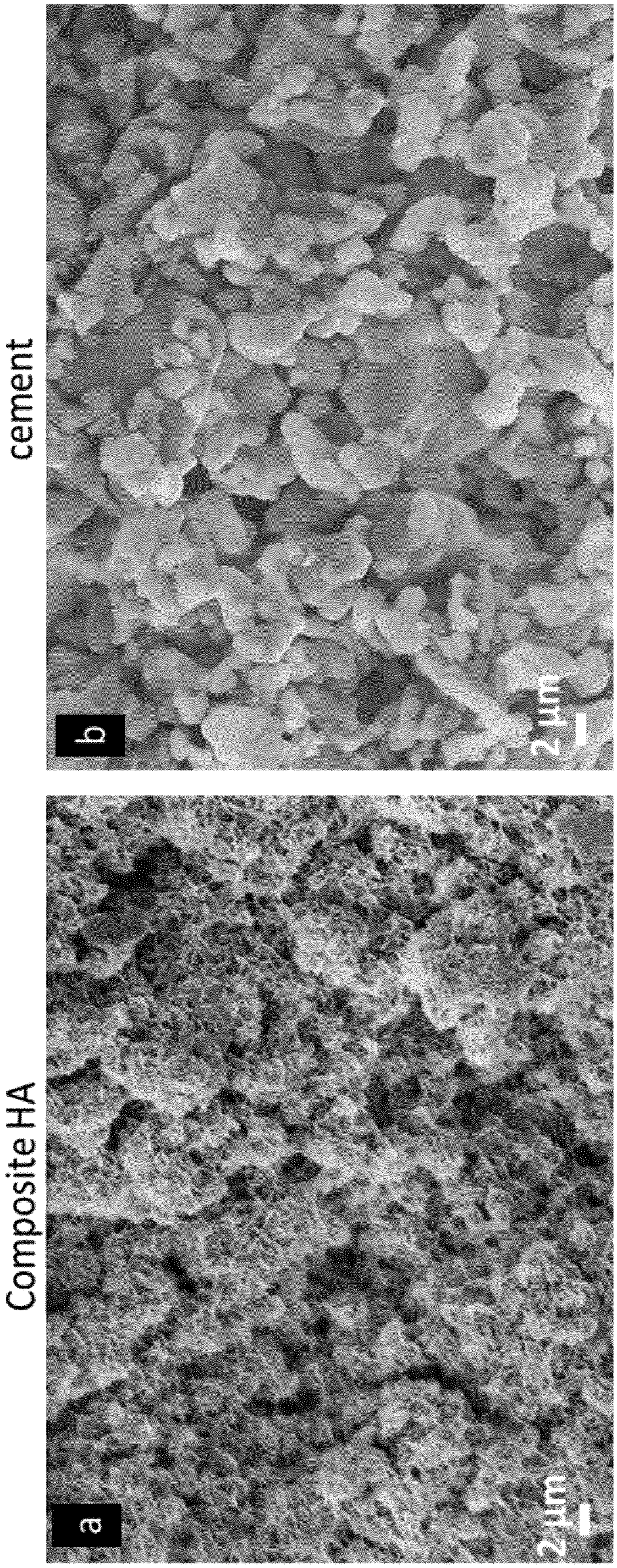

FIG. 4: scanning microscopy images of HA composite cement (A) and cement (B) after 48 h of immersion in NaCl (0.9%).

Figure 5:
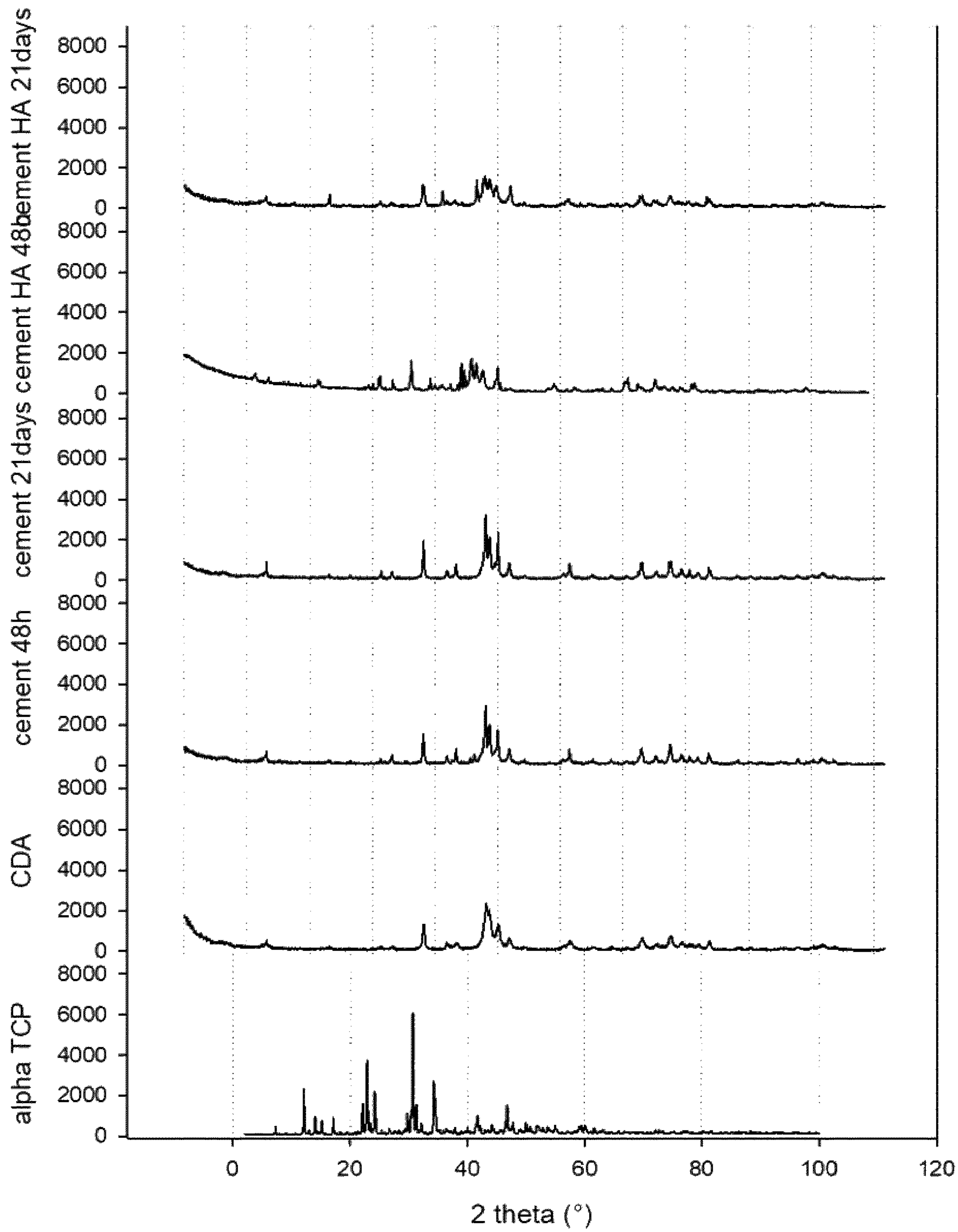

FIG. 5: diffractometer x ray of cement and HA composite cement after 48 h and 21 days of immersion in a saline solution.

Figure 6:
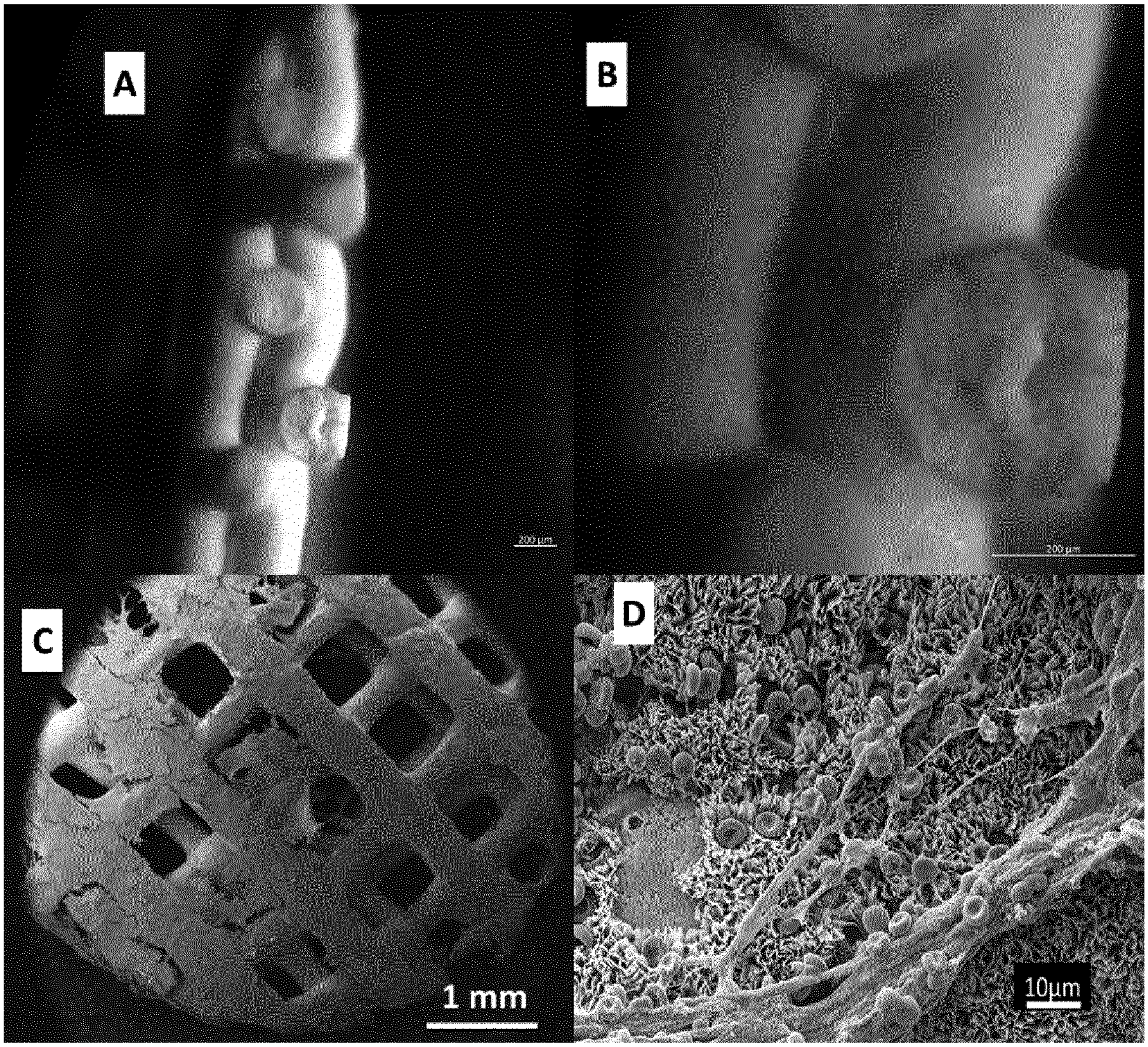

FIG. 6: HA composite HA printed with a pneumatic extrusion process (CellInk) through a 25 g (250 μm) diameter of needle (A, B, C). A disk of 5 mm of diameter, and 1 mm of depth (4 layers) was pretreated with total bone marrow during (40 min) (C). Scanning electronic microscopy image of the materials seeded with Total bone marrow (D).

Figure 7:
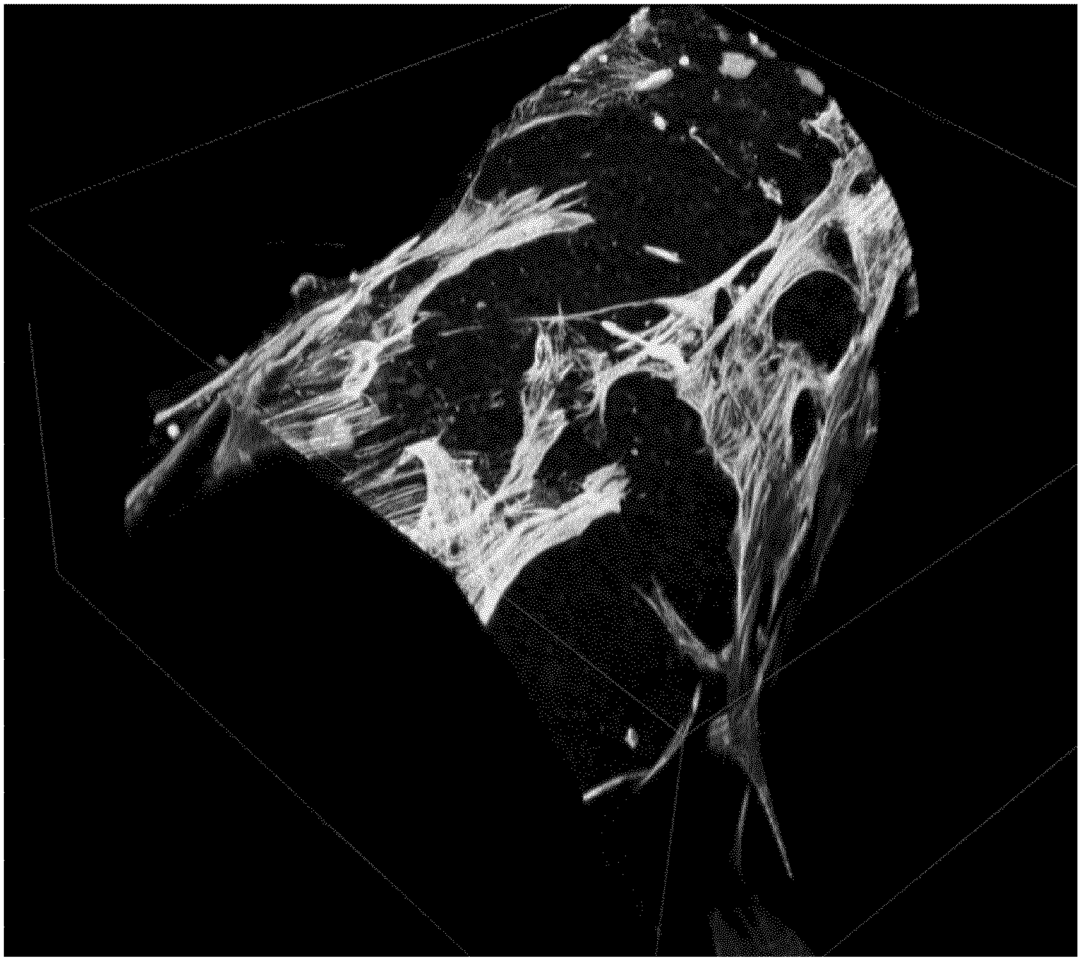

FIG. 7: confocal microscopy image of MSC after 16 days seeded on the 3D printed HA composite cement and labelled with phalloidin.

Figure 8:
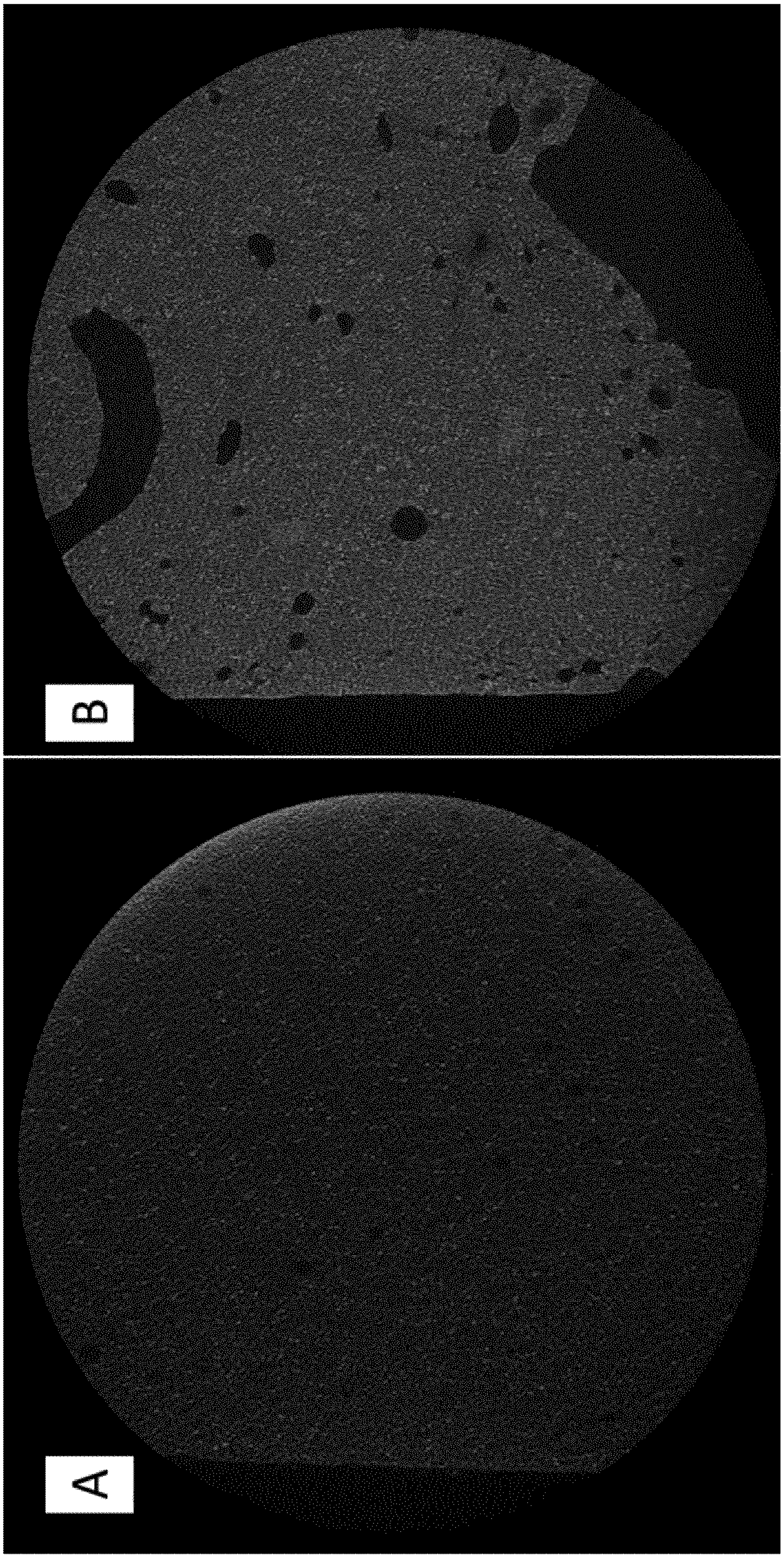

FIG. 8: microscannotomography of cement (A) and HA composite cement (B)

Figure 9:
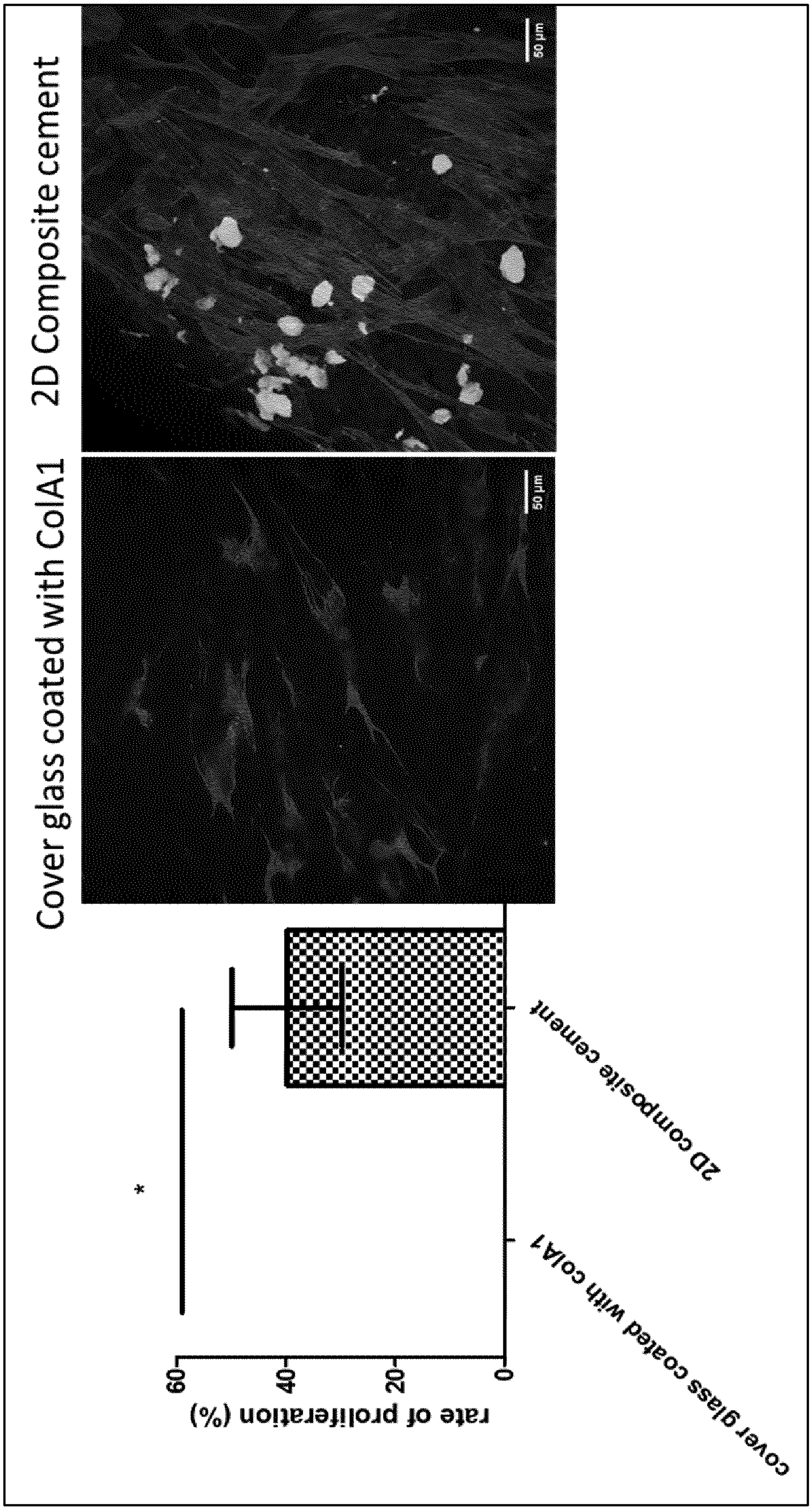

FIG. 9: mesenchymal stem cells seeded on cover glass coated with collagen I or on the HA composite cement labelled with the EDU imaging kit.

FIG. 10: Thixotropic loop of cement, HA composite cement and physical gel of HA.

FIG. 11: cyclic strain on cement, HA cement composite and gel.

FIG. 12: absolute viscosity ($\eta_0$) of the hyaluronic acid gel and the HA composite cement measured by CROSS equation (A) flow ramp of cement, gel and HA composite cement (B), curve of threshold fluid (C), measure of the threshold deformation (D).

Figure 13:
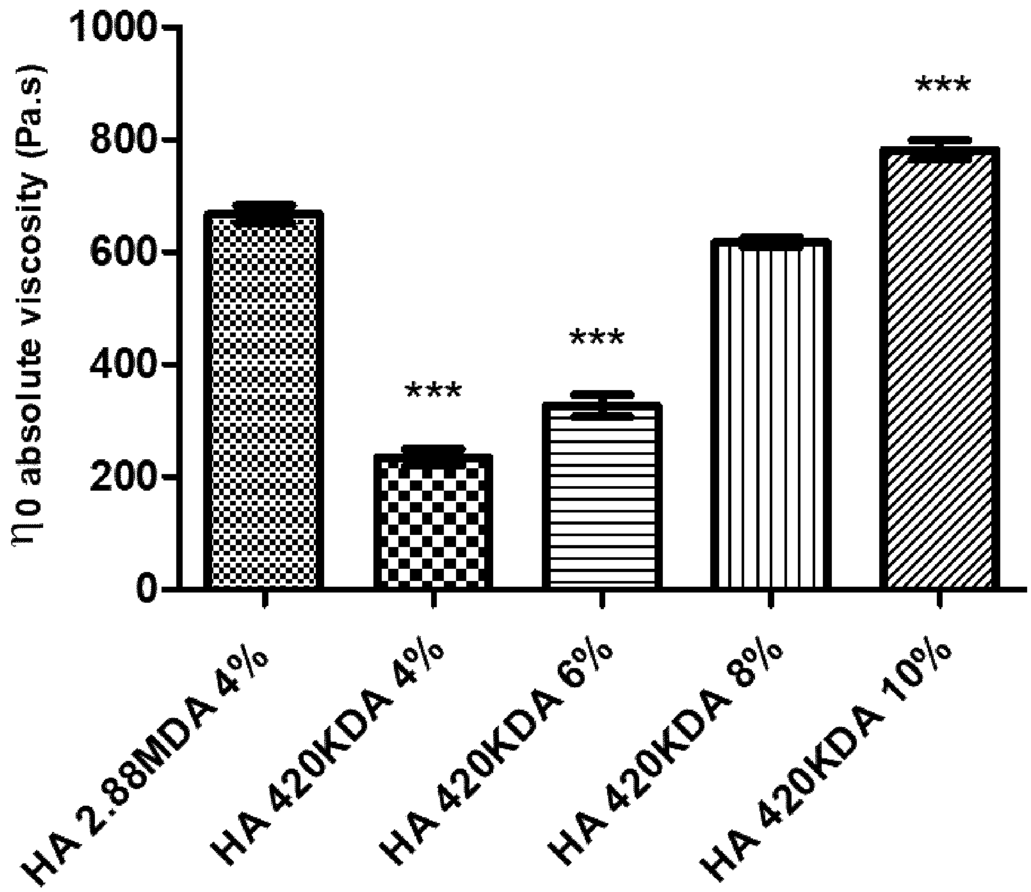

FIG. 13: absolute viscosity of different molecular weight and concentration of hyaluronic acid gels.

Figure 14:
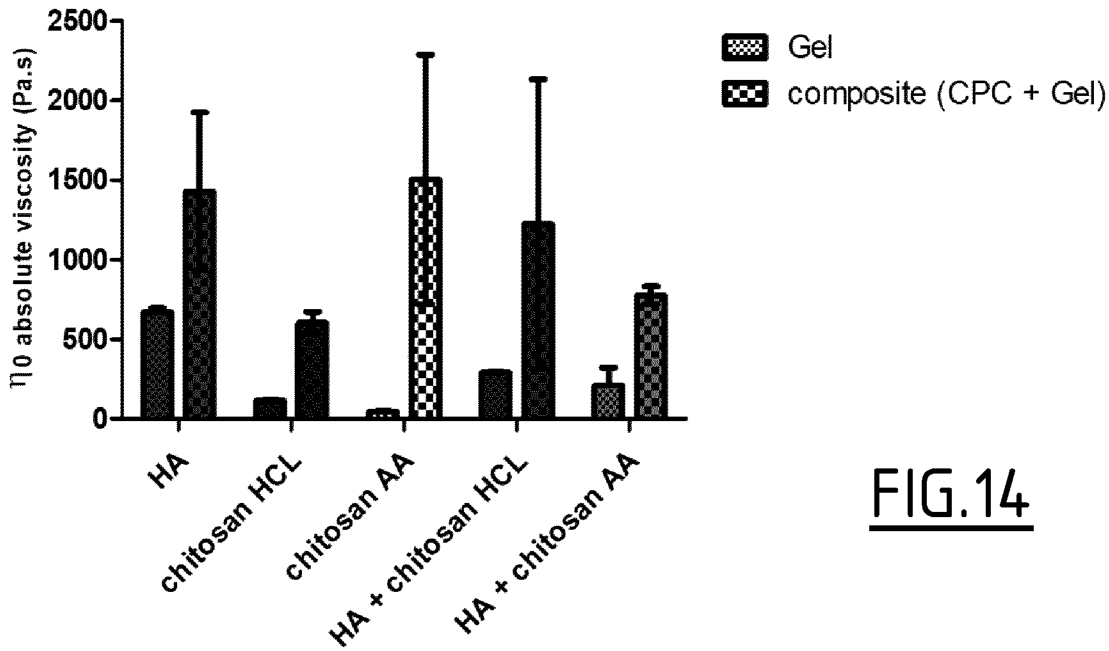

FIG. 14: flow ramp of different gels (dooted curves) and flaw ramp of different composite formulations (continuous curve) performed with the blending of cement with either chitosan dissolved in acidic solution of acetic acid (AA) or hydrochloric acid (HCL) or with hyaluronic acid dissolved in a glucose solution.

Figure 15:
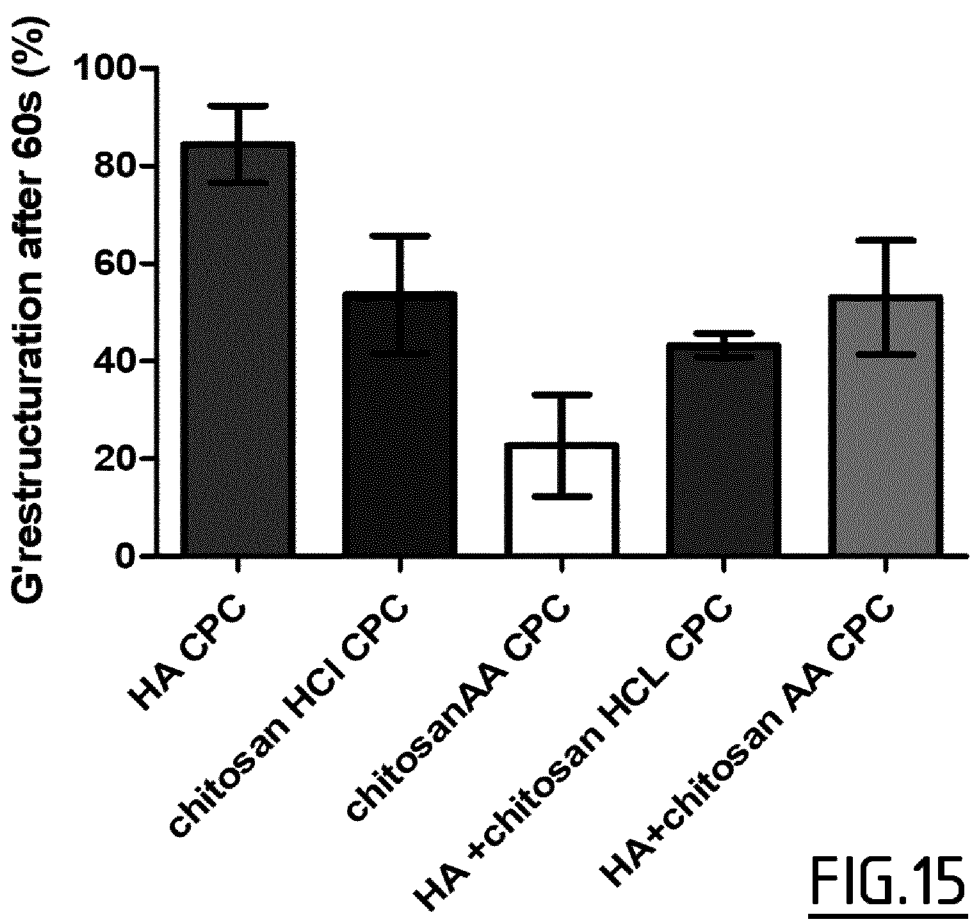

FIG. 15: cyclic strain of different composite formulations performed with the blending of cement with either chitosan dissolved in acidic solution of acetic acid (AA) or hydrochloric acid (HCL) or with hyaluronic acid dissolved in a glucose solution.

Figure 16:
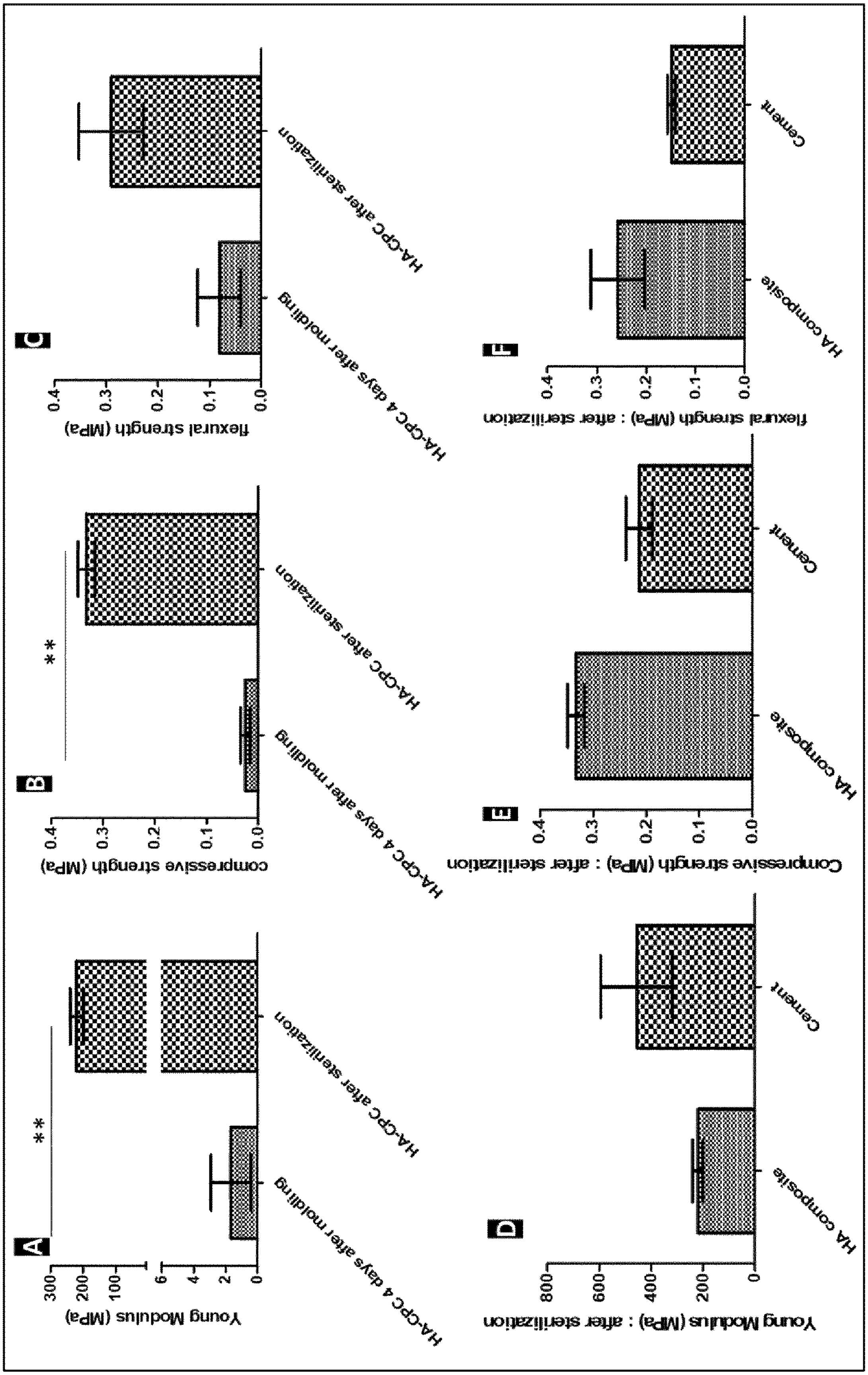

FIG. 16: young modulus of cement and HA composite cement was measured before and after the sterilization (A, D), compressive strength of cement and HA composite cement was measured before and after the sterilization (B, E), flexural strengths of cement and HA composite cement was measured before and after the sterilization (C, F).

Figure 17:
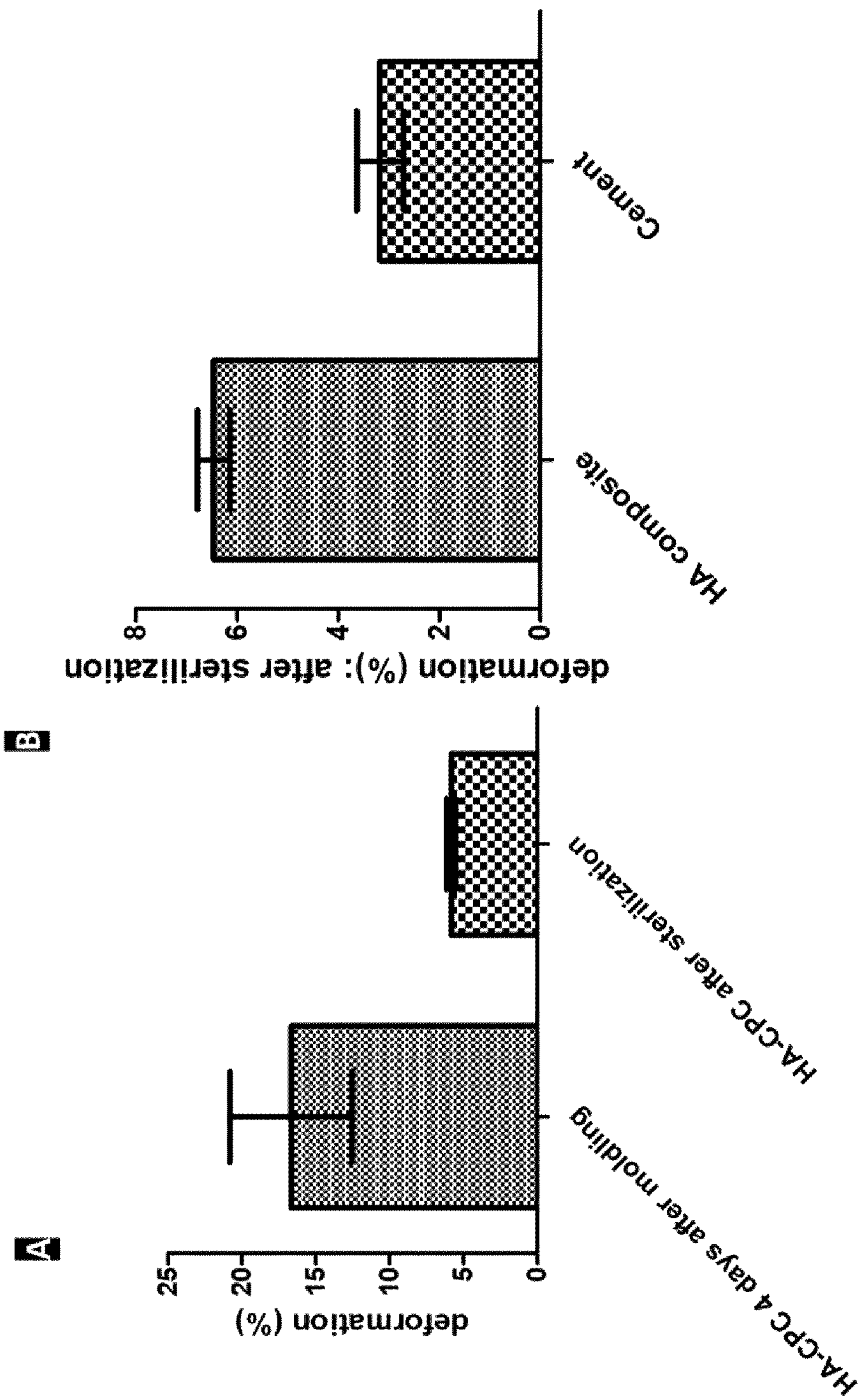

FIG. 17: deformation of HA composite and cement before and after sterilization.

EXAMPLES

Metabolic Activity

Methodology

Disks of 2 $cm^2$ of a composite cement of hyaluronic acid according to the invention were molded in order to fill a culture plate of 24 well. Fibroblast cell line L929 was seeded directly on the disk at a density of 50 000 cells by disk.

The sample (composite cement of hyaluronic acid L/P=2/3) were compared to the reference (phosphocalcic cement dissolved in the phosphate solution $Na_2HPO_4$ at the ratio L/P=2/3).

After 24 h and 3 days, the supernatant of the cell culture media was collected to perform CCK8 test (cell counting kit 8, sigma aldrich) regarding the provider specifications.

Results

More metabolic activity of fibroblast seeded on the composite cement of hyaluronic acid than on cement reference (the same ratio of physical gel of hyaluronic acid replace by a phosphate buffer) were found.

Cell Adhesion: 2D Culture

Methodology

Human mesenchymal stem cells were seeded on disks of 2 $cm^2$ making with the composite cement of hyaluronic acid of the invention at a density of 100 000 cells by disks. After 16 days of culture (FIG. 1) or 4 days (FIG. 2), cells were fixed with 4% paraformaldehyde for 10 min at room temperature then rinsed with BPS buffer. Cells were permeabilized with triton 0.1% for 3-5 min at room temperature. After rinsing with PBS buffer, aspecific site of protein cells were blocked with a solution of bovine serum albumine 1% for 20 min at room temperature.

Primary antibody of rabbit vinculin polyclonal (Product #PA5-29688 Thermofisher Scientific) at 1/300 in 0.1% BSA and incubated overnight at 4 degree celsius and then labeled with donkey anti-Rabbit IgG (H+L) Superclonal™ secondary antibody, Alexa Fluor® 568 conjugate (life technology) at a dilution of 1:1000 for 45 minutes at room temperature. Then alexa fluor 488 phalloidin (Thermofisher) dissolve 1/1000 in BSA 0.1% were added on cells for 30 min. Confocal macroscope were used for taking photographies.

Results

Over the cover slips coated with Col1, cells did not express as much as Vinculin than cells on composite cement of hyaluronic acid. This let suppose that hyaluronic acid, the main glycosaminoglycan of the extra cellular matrix improve cell adhesion on the composite cement of hyaluronic acid according to the invention (FIG. 1).

After 4 days MSC well attached and adhered either on cement or HA composite cement (FIG. 2). Nevertheless it is worth to note that the morphology of cells is different regarding the nature of the material. MSC is better spread on HA composite cement with larger and more numerous filopodes.

Viability

Methodology

A live and dead labeling (Molecular probes invitrogen) was performed, according to the provider specification, on fibroblast cell line L929 seeded either on cement (L/P=2/3) or on the composite cement of hyaluronic acid of the invention (L/P=2/3). Viability was determined by counting the living cells that metabolize the cleaving of calcein AM (green cells) and the dead cells expressing Ethidium homodimer −1.

Results

A non-inferiority result was find between cell viability on cement and on the composite cement of hyaluronic acid. The rate of viability is superior to 90% (FIG. 3).

Bioactivity

Methodology

Composite cement of hyaluronic acid (L/P=2/3) and cement (L/P=2/3) materials were immerged in a solution of NaCl 0.9% during 48 h. After driying in a dessicator the materials was metallized and observed by scanning electronic microscopy imaging.

Results

Nanoscale needle of apatite can be observed at the surface of HA composite cement (FIG. 4). This microstructure is mimicking the structure of the natural bone and contribute to improve cell adhesion onto the surface of the materials and osseointegration of the material when implanted.

Chemical composition

Methodology

HA composite cement (L/P=2/3) and cement (L/P=2/3) were molded and immerged in a saline solution (NaCl 0.9%) during 48 h and 21 days. After this different time point of kinetics the materials were dried in a desiccator during one night. The cement and HA composite cement were crushed and analyzed by diffractometer X ray.

Results

From 48 h it is possible to note the disappearance of the main peaks characterizing the α-TCP while the main peaks characterizing the calcium deficient apatite (CDA) appear (FIG. 5). This chemical composition is close to the mineral phase of the natural bone.

3D Printing: Total Bone Marrow and Mesenchymal Stem Cells Adhesion

Methodology

HA composite cement paste was loading into a syringe to be extruded by a pneumatic extrusion process through a 25 G (250 μm) of diameter needle.

Implant of 5 mm of diameter and 1 mm of depth was design (4 layers) with a prismatic interconnected porosity.

The implants was pretreated with total bone marrow during 40 min. After this implant was fixed with glutaraldehyde (4%) and different bath of acetone of increasing concentration (30%, 50%, 70%, 90%, 100%). Then bypassing the critical point of $CO_2$ was realized. Implant was metallized and observed by scanning electron microscopy imaging (FIG. 6)

MSC were seeded on 3D printed implants. After 16 days cells were fixed with PFA 4%, permeabilized with Triton (0.1%) and aspecific site blocked with a bovine serum albumin 4%. Then phalloidin (thermofisher 1/1000) was used to labelled actin fibres (FIG. 7).

Results

It is possible to observe how cells can migrated into the internal structure of the 3D printed implant. Cells attached and adhere on the printed filament.

Intrinsic Closed Mesoporosity

Methodology

Cement prepared with αTCP powder and phosphate buffer (L/P=2/3) or with αTCP powder and a physical gel of hyaluronic acid (L/P=2/3) were molded. After setting, the bar of the cement was break to analyze the internal microstructure thanks to microscanner imaging.

Results

Results are shown on FIG. 8.

A closed porosity can be observed after blending the cement with a visqueous gel of hyaluronic acid.

On cement only the intrinsec closed microporosity of 100 μm is observed.

Proliferation

Methodology

A click imaging EDU (thermofisher) was used to study the proliferation. Experience was realized according to the specification of the provider. Only proliferating cells can integrated the EDU into the DNA of the nuclei of cells and catabolism the cleavage of the fluorescent probe allowing a blue fluorescent.

Proliferation was measured by counting the numbers of cells metabolizing the click reaction by expressing a blue fluorescent compared to the total number of cells.

Results

After 16 days of culture, cells are able to keep on proliferating only on the composite HA cement (FIG. 9).

Rheology

Methodology

Rheological behavior of physical gel or composite cement was analyzed using a rheometer (RS300) thanks a flate and striated geometry and plate of 2 mm. Different measurement were realized

- thixotropy loop: a shear rate of 0 to 100 Pa/s was applied during 60 s then the shear rate has decreased from 100 to 0 Pa/s. The area of the curve can be measured thanks the Rheowin data software. Higher the area of the curve is higher the material is consider as thixotrope.
- cyclic strain: deformation of 5% during 1 min was applied. Then the rate of deformation was increased up to 100% during 160 s. Afterward the deformation rate come-back to the starting point.

flow curve: a shear rate of 0-100 Pa/s was applied to folow the evolution of the viscosity.

Results

The cement (L/P=2/3) is not thixotrope compared to HA gel and the HA composite cement (L/P=2/3). Adding of HA gel to replaced the phosphate buffer make the material thixotrope.

Results are shown on FIGS. 10, 11 and 12.

During higher deformation solid modulus of HA gel and HA composite decrease. At the end of the deformation solid modulus of HA gel and HA composite start to be restored. This behavior of the materials is compatible with the characteristics expected for printing.

Cement (L/P=2/3) is still liquid and start to flow from the shear rate is applied. When phosphate buffer is replaced by physical gel of HA it can be observed the behavior of a newtonien fluid at the beginning of the shear rate applied. The first part of the curve is still linear (the viscosity is independent of the deformation applied) and start to decrease (pseudoplastic region) meaning that the material is a threshold fluid. The rate of the deformation to be applied to start the flowing of the materials was measure by calculating the max of the curve of the shear rate regarding the rate of deformation (C).

A deformation of 3.375% for gel and 3.680% for the composite (D) were obtained. These rates of deformation are compatible with the strength required to extrude the paste through a 3D printer.

Cross equation allowed to measure the absolute viscosity of HA gel and HA composite cement. The viscosity of the composite cement is higher than viscosity of physical gel (A).

The absolute viscosity of lower molecular weight of hyaluronic acid can be similar to that of a higher molecular weight when increasing the concentration of the lower molecular weight of hyaluronic acid (FIG. 13).

All the gels and composite formulations are rheofluidifiant/pseudoplastic (their viscosity decreased under the shear rate imposed). Cross equation allows to measure the absolute viscosity and displayed an increasing of viscosity of formulations when gel is blending with cement (composite) (FIG. 14).

All the formulations are self-healing with a beginning of restructuration at the end of the higher rate of deformation (FIG. 15).

Mechanical Tests

Methodology

HA composite cement and cement L/P=2/3 was molded in a cylindrical mold (12 mm of length and 6 mm od diameter) for compressive tests or molded in rectangular mold (38*38*6 mm) for flexural tests. Thanks to a texture analyzer, the mechanical tests were applied.

Young modulus was calculated by calculating the slope at the origin of the curve.

Flexural strength was measured by calculating the breaking point force under 3 points flexion.

Compressive strength was measured by calculating the breaking point force under compression.

Deformation was estimated by calculating the lenght of the material at the breaking point force under compression.

Results

Results are shown on FIGS. 16 and 17.

The sterilization increases the mechanical properties of the HA composite cement. The young modulus of cement is higher than the composite because it is less elastic/deformable. Nevertheless the compressive strength and flexural strength of the composite is higher than those of the cement because the composite is more deformable (FIG. 17). All the mechanical results are in the range of those found for cancellous natural bone.

CONCLUSION

The inventors of the present invention have been able to develop a 3D printed formulation that meets all the mechanical, biological and regulatory requirements for bone repair (injectable, printable, cohesive, ductile, biocompatible, biodegradable, sterilizable, certified).

The invention claimed is:

1. A method for 3D printing comprising the step of printing a formulation comprising a phosphocalcic cement and a physical and/or covalent hydrogel of polysaccharides.

2. The method according to claim 1, wherein said polysaccharides are hyaluronic acid and/or chitosan.

3. The method according to claim 1, wherein said hydrogel is a physical hydrogel.

4. The method according to claim 1, wherein said cement is a tricalcium phosphate cement.

5. The method according to claim 1, wherein the ratio hydrogel/cement is of 2:3 w/w.

6. The method according to claim 1, wherein said hydrogel is a physical hydrogel comprising from 2 to 4% w/v of hyaluronic acid and/or chitosan.

7. The method according to claim 1, wherein said hydrogel is a covalent hydrogel of silated hyaluronic acid and/or silated chitosan.

8. The method according to claim 1, for bone regeneration and/or bone repair.

9. The method according to claim 1 in the context of vertical bone augmentation, complex geometries, large critical size bone defects, or following congenital diseases or to fill bone defects following tumor resections.

10. The method according to claim 1 for 3D printing of bone implants.

11. The method according to claim 1, wherein the phosphocalcic cement is prepared with α-TCP.

12. A kit for 3D printing of bone implants comprising:

(i) a phosphocalcic cement; and (ii) a physical and/or covalent hydrogel of polysaccharides.

13. A method to prepare a formulation for 3D printing comprising a step of mixing a phosphocalcic cement and a physical and/or covalent liquid hydrogel precursor of polysaccharides.

14. An implant comprising a formulation as defined in claim 1.

15. Implant according to claim 14, further comprising active molecules.

16. The implant according to claim 14, further comprising growth factors and/or cells.

17. A method for bone repair and/or bone regeneration comprising:

(i) preparing a formulation comprising a phosphocalcic cement and a physical and/or covalent hydrogel of polysaccharides/or chitosan;

(ii) 3D printing of said formulation to form an implant; and optionally (iii) inserting the implant obtained further to step (ii) in a bone cavity.

18. A method according to claim 17, wherein the cement and the hydrogel are sterilized in a sterile environment or wherein the implant is sterilized before insertion.

19. The method for bone repair and/or bone regeneration according to claim 17, comprising preparing a formulation comprising α-TCP powder, and a physical and/or covalent hydrogel of polysaccharides as in step (i).

20. The method according to claim 17, wherein the hydrogel comprises hyaluronic acid and/or chitosan.

* * * * *